US009486410B2

(12) United States Patent
Perlman et al.

(10) Patent No.: US 9,486,410 B2
(45) Date of Patent: Nov. 8, 2016

(54) PHARMACEUTICAL COMPOSITIONS OF AMORPHOUS DISPERSIONS OF DRUGS AND LIPOPHILIC MICROPHASE-FORMING MATERIALS

(75) Inventors: Michael E. Perlman, Old Saybrook, CT (US); Ravi M. Shanker, Groton, CT (US); Walter C. Babcock, Bend, OR (US); Dwayne Thomas Friesen, Bend, OR (US); Mark D. Rabenstein, Bend, OR (US); Dan Tod Smithey, Bend, OR (US)

(73) Assignee: Bend Research, Inc., Bend, OR (US)

( * ) Notice: Subject to any disclaimer, the term of this patent is extended or adjusted under 35 U.S.C. 154(b) by 802 days.

(21) Appl. No.: 11/924,988

(22) Filed: Oct. 26, 2007

(65) Prior Publication Data
US 2008/0063708 A1 Mar. 13, 2008

Related U.S. Application Data

(63) Continuation of application No. 10/355,747, filed on Jan. 31, 2003, now abandoned.

(60) Provisional application No. 60/354,081, filed on Feb. 1, 2002.

(30) Foreign Application Priority Data

Jan. 28, 2003 (WO) .................. PCT/IB03/00335

(51) Int. Cl.
*A61K 9/20* (2006.01)
*A61K 47/38* (2006.01)
*A61K 9/14* (2006.01)
*A61K 9/16* (2006.01)

(52) U.S. Cl.
CPC ............. *A61K 9/146* (2013.01); *A61K 9/1652* (2013.01); *A61K 9/145* (2013.01); *A61K 9/1617* (2013.01)

(58) Field of Classification Search
None
See application file for complete search history.

(56) References Cited

U.S. PATENT DOCUMENTS

| 4,343,789 A | 8/1982 | Kawata et al. |
| 4,581,232 A | 4/1986 | Peters et al. |
| 4,711,774 A | 12/1987 | Denick, Jr. et al. |
| 4,716,033 A | 12/1987 | Denick, Jr. |
| 4,717,565 A | 1/1988 | Denick, Jr. |
| 4,719,228 A * | 1/1988 | Rawlins ........................ 514/456 |
| 4,772,627 A | 9/1988 | Matsui et al. |
| 4,835,186 A | 5/1989 | Reuter et al. |
| 4,973,469 A | 11/1990 | Mulligan et al. |
| 5,008,114 A | 4/1991 | Lovrecich |
| 5,015,479 A | 5/1991 | Mulligan et al. |
| 5,128,142 A | 7/1992 | Mulligan et al. |
| 5,281,420 A | 1/1994 | Kelm et al. .................... 424/452 |
| 5,449,521 A | 9/1995 | Lovrecich |
| 5,505,959 A | 4/1996 | Tachon et al. |
| 5,580,546 A | 12/1996 | Ser et al. ........................ 424/59 |
| 5,610,193 A | 3/1997 | Al-Razzak et al. |
| 5,626,878 A | 5/1997 | Garay |
| 5,700,485 A | 12/1997 | Berde et al. .................. 424/501 |
| 5,723,269 A | 3/1998 | Akagi et al. .................. 424/497 |
| 5,759,997 A * | 6/1998 | Cavanak ..................... 514/20.5 |
| 5,773,021 A | 6/1998 | Gurtler et al. |
| 5,925,645 A | 7/1999 | Schmidt et al. |
| 5,932,587 A | 8/1999 | Schmeck et al. |
| 5,993,858 A | 11/1999 | Crison et al. ................. 424/490 |
| 6,004,973 A | 12/1999 | Guitard et al. ............... 514/291 |
| 6,015,797 A | 1/2000 | Camborde et al. |
| 6,063,788 A | 5/2000 | Brandes et al. |
| 6,069,148 A | 5/2000 | Schmidt et al. |
| 6,107,290 A | 8/2000 | Woo |
| 6,121,330 A | 9/2000 | Muller-Gliemann et al. |
| 6,127,383 A | 10/2000 | Schmidt et al. |
| 6,140,342 A | 10/2000 | Goldstein et al. |
| 6,140,343 A | 10/2000 | DeNinno et al. |
| 6,147,089 A | 11/2000 | DeNinno et al. |
| 6,147,090 A | 11/2000 | DeNinno et al. |
| 6,191,162 B1 | 2/2001 | Byrd et al. ..................... 514/440 |
| 6,197,781 B1 | 3/2001 | Guitard et al. ............... 514/291 |
| 6,197,786 B1 | 3/2001 | DeNinno et al. |
| 6,207,671 B1 | 3/2001 | Schmidt et al. |
| 6,254,889 B1 | 7/2001 | Kigoshi et al. ............... 424/487 |
| 6,264,981 B1 | 7/2001 | Zhang et al. ................. 424/451 |
| 6,280,770 B1 | 8/2001 | Pather et al. ................. 424/465 |

(Continued)

FOREIGN PATENT DOCUMENTS

| EP | 0179583 | * | 4/1986 |
| EP | 0429187 | | 1/1994 |

(Continued)

OTHER PUBLICATIONS

Abd El-Gawad, .A.H., et al., "Effect of Surfactant Incorporation Techniques on Sulphamethoxazole Suppository Formulations", Pharmazie, 1988, pp. 624-627, vol. 43.
Takada, K., et al., "Enteric Solid Dispersion of Cyclosporin A (CyA) Having Potential to Improve Availability of CyA in Rabbit", Chem. Pharm. Bull., 1989, pp. 2542-2544, vol. 37, No. 9.
Charman, S.A., et al., "Self-Emulsifying Drug Delivery Systems: Formulation and Biopharmaceutic Evaluation of an Investigational Lipophilic Compound", Pharmaceutical Research, 1992, vol. 9, No. 1.
Saers, E.S., et al., "Physicochemcial Aspects of Drug Release. XVI. The Effect of Storage on Drug Dissolution from Solid Dispersions and the Influence of Cooling Rate and Incorporation of Surfactant", International Journal of Pharmaceutics, 1993, pp. 105-118, vol. 90.
Sheen, P.C., et al., "Formulation Studies of a Poorly Water-Soluble Drug in Solid Dispersions to Improve Bioavailability", International Journal of Pharmaceutics, 1995, pp. 221-227, vol. 118.
Gershanik, T., et al., "Self-Dispersing Lipid Formulations for Improving Oral Absorptions of Lipophilic Drugs", 2000, pp. 179-188, vol. 50.

(Continued)

Primary Examiner — Robert A Wax
Assistant Examiner — Danah Al-Awadi
(74) Attorney, Agent, or Firm — Klarquist Sparkman, LLP

(57) ABSTRACT

A pharmaceutical composition comprises a solid amorphous dispersion comprising a low-solubility drug and a concentration-enhancing polymer and a lipophilic microphase-forming material. Alternatively, a solid amorphous dispersion comprising a low-solubility drug and a concentration-enhancing polymer is co-administered with a lipophilic microphase-forming material to an in vivo use environment.

14 Claims, No Drawings

(56) References Cited

U.S. PATENT DOCUMENTS

| | | | |
|---|---|---|---|
| 6,291,477 B1 | 9/2001 | Schmidt et al. | |
| 6,294,192 B1 | 9/2001 | Patel et al. | 424/451 |
| 6,310,075 B1 | 10/2001 | DeNinno et al. | |
| 6,312,704 B1 | 11/2001 | Farah et al. | 424/401 |
| 6,316,497 B1 | 11/2001 | Liu et al. | 514/475 |
| 6,362,198 B1 | 3/2002 | Goldstein et al. | |
| 6,426,365 B1 | 7/2002 | Shinkai et al. | |
| 6,436,441 B1 | 8/2002 | Sako et al. | 424/488 |
| 6,548,555 B1 * | 4/2003 | Curatolo et al. | 514/772.4 |
| 6,602,523 B1 | 8/2003 | Joshi | |
| 2001/0009677 A1 | 7/2001 | Bruce et al. | |
| 2001/0044409 A1 | 11/2001 | Ghebre-Sellassie et al. | 514/26 |
| 2001/0053791 A1 | 12/2001 | Babcock | |
| 2002/0006443 A1 * | 1/2002 | Curatolo et al. | 424/486 |
| 2002/0103225 A1 | 8/2002 | Curatolo et al. | |
| 2003/0022944 A1 | 1/2003 | Gumkowski et al. | |
| 2003/0054037 A1 * | 3/2003 | Babcock | A61K 9/143 424/486 |
| 2003/0099708 A1 | 5/2003 | Rowe et al. | |
| 2003/0129239 A1 | 7/2003 | Goldshtein | |

FOREIGN PATENT DOCUMENTS

| | | | |
|---|---|---|---|
| EP | 0440702 | 4/1994 | A61K 9/18 |
| EP | 0852140 | 7/1998 | A61K 9/00 |
| EP | 0901786 | 3/1999 | A61K 9/14 |
| EP | 901786 A2 * | 3/1999 | |
| EP | 0943327 A1 | 9/1999 | |
| EP | 1027885 | 8/2000 | |
| EP | 1027886 | 8/2000 | |
| EP | 1027887 | 8/2000 | A61K 9/26 |
| EP | 1027888 | 8/2000 | A61K 9/26 |
| JP | 7-291854 | 11/1996 | |
| JP | 200016934 | 1/2000 | |
| SI | 9500059 | 8/1996 | |
| WO | WO 90/01329 A1 | 2/1990 | |
| WO | WO 9004962 | 5/1990 | A61K 9/18 |
| WO | WO 96/19239 | 6/1996 | |
| WO | WO9804528 | 2/1998 | |
| WO | WO 9831360 | 7/1998 | A61K 31/19 |
| WO | WO 9831361 | 7/1998 | A61K 31/215 |
| WO | WO9834920 | 8/1998 | |
| WO | WO9835937 | 8/1998 | |
| WO | WO9838167 | 9/1998 | |
| WO | WO9839299 | 9/1998 | |
| WO | WO 9906044 A1 * | 2/1999 | |
| WO | WO 9908660 | 2/1999 | A61K 9/14 |
| WO | WO9914174 | 3/1999 | |
| WO | WO9914204 | 3/1999 | |
| WO | WO9914215 | 3/1999 | |
| WO | WO9915487 | 4/1999 | |
| WO | WO 99/27946 A1 | 6/1999 | |
| WO | WO9940061 | 8/1999 | |
| WO | WO9941237 | 8/1999 | |
| WO | WO 0000179 | 1/2000 | A61K 9/14 |
| WO | WO0018721 | 4/2000 | |
| WO | WO0018723 | 4/2000 | |
| WO | WO0018724 | 4/2000 | |
| WO | WO0038722 | 7/2000 | |
| WO | WO 0057881 | 10/2000 | A61K 31/47 |
| WO | WO0100180 | 1/2001 | |
| WO | WO0110410 | 2/2001 | |
| WO | WO 0115664 | 3/2001 | A61K 9/00 |
| WO | WO 0130288 | 5/2001 | A61K 9/20 |
| WO | 0140190 | 6/2001 | |
| WO | WO 01/41765 A1 | 6/2001 | |
| WO | WO 01/42221 A1 | 6/2001 | |
| WO | 01/47495 | 7/2001 | |
| WO | WO 01/47498 A2 | 7/2001 | |
| WO | WO 01/47500 A1 | 7/2001 | |
| WO | WO 0147495 | 7/2001 | A61K 9/14 |
| WO | WO 0154667 | 8/2001 | A61K 9/14 |
| WO | WO 01/68055 A1 | 9/2001 | |
| WO | WO 0195939 | 12/2001 | A61K 47/32 |
| WO | WO0211710 | 2/2002 | |
| WO | WO 03/000238 A1 | 1/2003 | |
| WO | WO 03/004060 A1 | 1/2003 | |
| WO | WO03063833 | 8/2003 | |

OTHER PUBLICATIONS

Takada, K., et al., "Enteric Solid Dispersion of Ciclosporin A (CiA) Having Potential to Deliver CiA into Lymphatics", Chem. Pharm. Bull., 1989, pp. 471-474, vol. 37, No. 2.

Kerc et al., "Alternative solvent-free preparation methods for felodipine surface solid dispersions," Drug Development and Industrial Pharmacy, 24 (4), 359-363 (1998).

Kerc et al., "Use of hydrophilic carriers in enhancement of felodipine dissolution," Acta Pharm. Jugosl. 41, 259-265 (1991).

Kerc et al., "Dissolution study of felodipine solid dispersions," Acta Pharm. 43, 113-120 (1993).

Chowdary et al., "Enhcancement of Dissolution Rate of Meloxicam," Indian Journal of Pharmaceutical Sciences, Apr.-Mar. 2001, 150-154.

Monkhouse et al., "Use of adsorbents in enhcancement of drug dissolution I," Journal of Pharmaceutical Sciences 61, No. 9, 1430-1435 (1972).

Konno et al., "Physical and chemical changes of medicinals in mixtures with adsorbents in the solid state. I. Effect of vapor pressure of the medicinals on changes in crystalline properties," Chem. Pharm. Bul. 34 (1) 301-307 (1986).

Alsaidan, S.M. et al., "Improved dissolution rate of indomethacin by adsorbents", Drug Development and Industrial Pharmacy, 24(4), pp. 389-394, Apr. 1998.

A.Y. Gore et al., "Surface chemistry of colloidal silica and a possible application to stabilize aspirin in solid matrixes", Journal of Pharmaceutical Sciences, vol. 68, No. 2, pp. 197-202, Feb. 1979.

Daniels, R. et al., "The stability of drug adsorbates on silica", Drug Development and Industrial Pharmacy, 12(11-13), pp. 2127-2156, Jan. 1986.

JP-11246404 Patent Abstracts of Japan, Sep. 1999.

Katzhendler I. et al., "Crystalline properties of carbamazepine in sustained release hydrophilic matrix tablets based on hydroxypropyl methylcellulose", Journal of Controlled Release, 54, pp. 69-85, Jun. 1998.

Konno T. et al., "Physical and chemical changes of medicinals in mixtures with adsorbents in the solid state. III. Determination of vapor pressure of solid drugs by steam distillation", Chem. Pharm. Bull, 38:4, pp. 1032-1034, Apr. 1990.

Monkhouse, D.C. et al., "Use of adsorbents in enhancement of drug dissolution II", Journal of Pharmaceutical Sciences, vol. 61, No. 9, 1435-1441, Sep. 1972.

Oguchi, T et al., "Improved dissolution of Naproxen from solid dispersions with porous additives", Yakuzaigaku, vol. 57, No. 3, pp. 168-173, Sep. 1997.

Takenaka, H. et al., "Preparation of enteric-coated microcapsules for tableting by spray-drying technique and in vitro simulation of drug release from the tablet in GI tract", Journal of Pharmaceutical Sciences, vol. 69, No. 12, pp. 1388-1392, Dec. 1980.

Takeuchi, H. et al., "Spherical solid dispersion containing amorphous tolbutamide embedded in enteric coating polymers or colloidal silica prepared by spray-drying technique", Chem. Pharm. Bull., 35(9), pp. 3800-3806, Feb. 2, 1987.

Yamamoto K. et al., "Adsorption of pharmaceutical organic compounds onto porous materials", CRC Press, chapter 29, pp. 763-779, Jan. 21, 1999.

Data Sheet for European Application No. 03-700-435.5.

F. Lallemand et al., "A Water-Soluble Prodrug of Cyclosporine A for Ocular Application: A Stability Study," European Journal of Pharmaceutical Sciences, 26(2005) 124-129.

* cited by examiner

PHARMACEUTICAL COMPOSITIONS OF AMORPHOUS DISPERSIONS OF DRUGS AND LIPOPHILIC MICROPHASE-FORMING MATERIALS

This application Claims priority of U.S. Ser. No. 10/355,747, filed on Jan. 31, 2003, which claims priority to PCT Application No. PCT/IB03/00335, filed on Jan. 28, 2002, which claims priority to U.S. Provisional Ser. No. 60/354,081 filed on Feb. 2, 1002.

BACKGROUND OF THE INVENTION

The invention relates to pharmaceutical compositions comprising (1) a solid amorphous dispersion comprising a low-solubility drug and a concentration-enhancing polymer and (2) a lipophilic microphase-forming material that enhances the concentration of the drug in a use environment.

Low-solubility drugs often show poor bioavailability or irregular absorption, the degree of irregularity being affected by factors such as dose level, fed state of the patient, and form of the drug. Increasing the bioavailability of low-solubility drugs has been the subject of much research. Increasing bioavailability depends on improving the concentration of dissolved drug in solution to improve absorption.

It is well known that the amorphous form of a low-solubility drug that is capable of existing in either the crystalline or amorphous form may temporarily provide a greater aqueous concentration of drug relative to the equilibrium concentration obtained by dissolution of the drug in a use environment. Such amorphous forms may consist of the amorphous drug alone, a dispersion of the drug in a matrix material, or the drug adsorbed onto a substrate. It is believed that such amorphous forms of the drug may dissolve more rapidly than the crystalline form, often dissolving faster than the drug can precipitate from solution. As a result, the amorphous form may temporarily provide a greater-than equilibrium concentration of drug.

While such amorphous forms may show initially enhanced concentration of the drug in a use environment, nevertheless the improved concentration is often short-lived. Typically, the initially enhanced drug concentration is only temporary and quickly returns to the lower equilibrium concentration.

One approach to increase the bioavailability of low-solubility drugs has involved forming amorphous dispersions of drugs with polymers. Examples of attempts to increase drug concentration by forming a dispersion of the drug with a polymer include Nakamichi et al., U.S. Pat. No. 5,456,923, and Curatolo et al., EP 0901786A2.

It is known to mix surfactants with solid amorphous dispersions. Curatolo et al., EP 0901786A2 disclose that a component of the dispersion may be a surface-active agent such as a fatty acid and alkyl sulfonate, commercial surfactants such as benzethanium chloride, docusate sodium, and polyoxyethylene sorbitan fatty acid esters, and natural surfactants. Curatolo et al. state that such materials can advantageously be employed to increase the rate of dissolution by facilitating wetting, thereby increasing the maximum drug concentration and the degree of supersaturation attained, and also to inhibit crystallization or precipitation of drug by interacting with dissolved drug by mechanisms such as complexation, formation of inclusion complexes, formation of micelles or adsorbing to the surface of solid drug, crystalline or amorphous. Curatolo et al. state that these surface active agents may comprise up to 25% of the dispersion. In addition, Curatolo et al. also disclose that surface active agents may be present in compositions containing dispersions.

Nevertheless, what is still desired is a composition that may enhance the dissolution and/or bioavailability of poorly soluble drugs. These needs and others that will become apparent to one of ordinary skill are met by the present invention, which is summarized and described in detail below.

BRIEF SUMMARY OF THE INVENTION

The present invention overcomes the drawbacks of the prior art by providing a composition comprising (1) a solid amorphous dispersion comprising a low-solubility drug and a concentration-enhancing polymer and (2) a lipophilic microphase-forming material. The combination of a solid amorphous dispersion and a lipophilic microphase-forming material results in improved dissolved concentration of the drug in the aqueous use environment, and in some embodiments a surprising synergy. For a given dose of drug, the combination may either provide higher bioavailability with the same amount of concentration-enhancing polymer, or may provide the same bioavailability but with less concentration-enhancing polymer.

In another aspect of the invention, a solid amorphous dispersion comprising a low-solubility drug and a concentration-enhancing polymer is co-administered with a lipophilic microphase-forming material to an in vivo use environment. Another aspect of the invention comprises a kit comprising a solid amorphous dispersion comprising a low-solubility drug and a concentration-enhancing polymer and a lipophilic microphase-forming material.

The present inventors have found that the ability of a solid amorphous dispersion to enhance the concentration of drug in a use environment may be significantly improved by the addition of certain lipophilic microphase-forming materials. These lipophilic microphase-forming materials, when administered to an aqueous use environment such as the GI tract, form a plurality of small microphases, or so-called "lipophilic microphases." The lipophilic microphase-forming materials are chosen (1) to be water immiscible, (2) so that the drug has a high partition coefficient with respect to the lipophilic microphases, and (3) so that the resulting lipophilic microphases in the aqueous use environment are small.

Without wishing to be bound by any particular theory, the present inventors believe that when a composition of the present invention comprising a solid amorphous dispersion comprising a low-solubility drug and a concentration-enhancing polymer and a lipophilic microphase-forming material are introduced to a use environment such as the GI tract, the drug may be present in several different species. When the aqueous use environment is either the GI tract of an animal, or an in vitro use environment that simulates the GI tract of an animal, it is believed that at least five different drug species are formed: (1) free drug; (2) drug present within bile salt micelles that are naturally occurring in the GI tract; (3) polymer/drug assemblies; (4) precipitate; and (5) drug in lipophilic microphases.

As used herein, the term "free drug" refers to drug molecules which are dissolved in the aqueous solution and are generally either monomeric or clusters of no more than about 100 molecules. A "polymer/drug assembly" refers to a collection of polymer molecules and drug molecules which are physically associated to form an assembly or aggregate that is sufficiently small that it remains suspended in solution. "Precipitate" is a general term for any relatively large particulates that form and fall out of solution, either naturally or upon centrifugation. Such precipitate may comprise one or more or all of the following forms: (1) crystalline drug; (2) amorphous drug; and/or (3) a mixture of drug and polymer that is present as particles that are sufficiently large so as to drop out of solution (typically greater than about 5 to 10 microns in average diameter). As used herein, the term "total dissolved drug" refers to the concentration of drug in a use environment that is not present in precipitate. Thus, "total dissolved drug" refers to drug that is present as free drug, drug within bile salt micelles, drug in polymer/drug assemblies, and drug in the lipophilic microphases.

It is desired to increase the free drug concentration in the GI tract because, in general, primarily free drug is directly absorbed from the GI tract into the blood. The absorption rate of a drug from the GI tract to the blood is therefore generally proportional to the free drug concentration at the intestinal membrane surface. Drug present in the other species generally must first convert to the free drug form in order to be absorbed.

The present invention provides one or more of the following advantages over prior methods for enhancing the concentration and bioavailability of low-solubility drugs. The lipophilic microphases are capable of sufficiently solubilizing the drug in the use environment to enhance bioavailability. In some cases, the lipophilic microphases are thought to be (1) highly mobile, meaning that they may diffuse more rapidly throughout the use environment than precipitate; and (2) labile, meaning that the drug may rapidly convert back and forth between the lipophilic microphases and free drug. It is believed that the lipophilic microphases may be more mobile than the polymer/drug assemblies. Because the lipophilic microphases solubilize the drug, the lipophilic microphases may reduce the formation of drug precipitate and increase the amount of total dissolved drug. The lability of the lipophilic microphases may also increase the rate of resupply of free drug in the use environment. As free drug is absorbed, drug present in the lipophilic microphases may rapidly convert to free drug, thus maintaining a sustained free drug concentration. When the lipophilic microphases are small, their high mobility may also increase the rate of drug absorption by the intestines by increasing the transport rate of the drug through the unstirred boundary layer adjacent to the intestinal wall. In combination, these properties may greatly enhance the rate and extent of drug absorption (e.g., bioavailability).

In addition, the compositions may also have the advantage of providing more regular absorption between the fed and fasted state of a patient. A problem when dosing low-solubility, lipophilic drugs is that the absorption of the drug may vary widely between the fed and fasted state of the patient. As previously noted, bile-salt micelles may be present in the GI tract. These micelles can behave in a similar way as the lipophilic microphase-forming materials of the present invention. It is believed that drug can readily partition into such bile-salt micelles, and drug in bile-salt micelles is readily absorbable because it is labile and the micelles are highly mobile.

It is well known in the art that in the fed state, the concentration of bile-salt micelles present in the GI tract is greater than the concentration present in the fasted state. The inventors believe that this difference in the concentration of bile-salt micelles in the GI tract in the fed versus fasted state may account, at least in part, for the fed/fasted differences in bioavailability observed for many pharmaceutical compositions. The compositions of the present invention comprising a solid amorphous dispersion and a lipophilic microphase-forming material may minimize this fed/fasted difference in bioavailability. The compositions tend to equalize the amount of drug present in highly labile, highly mobile species between the fed and fasted state, and thus provide a more uniform bioavailability between the fed and fasted state.

The foregoing and other objectives, features, and advantages of the invention will be more readily understood upon consideration of the following detailed description of the invention.

DETAILED DESCRIPTION OF THE PREFERRED EMBODIMENTS

The present invention provides in one aspect a composition comprising (1) a solid amorphous dispersion comprising a low-solubility drug and a concentration-enhancing polymer, and (2) a lipophilic microphase-forming material. The lipophilic microphase-forming material may either be present in the dispersion itself, may be mixed with the dispersion, or may be separate from but co-administered with the dispersion. Suitable lipophilic microphase-forming materials, drugs and polymers, and methods for making the compositions, are discussed in more detail below.

Lipophilic Microphase-Forming Materials

The lipophilic microphase-forming material may comprise a surfactant and/or a lipophilic material. Thus, as used herein, the "lipophilic microphase-forming material" is intended to include blends of materials in addition to a single material. The lipophilic microphase-forming material must (1) be water immiscible (2) be capable of forming a plurality of small lipophilic microphases in the use environment and (3) have a relatively high partition coefficient for the drug in the use environment.

The lipophilic microphase-forming material must be "water immiscible," meaning that the material when administered as prescribed herein to an in vivo aqueous use environment exceeds its solubility as solvated molecules thus requiring the formation of a second phase. Ideally such a second phase takes the form of a large number of small phases such as micelles or a microemulsion. The lipophilic microphase is a separate phase in the aqueous use environment; the separate phase ranging from extremely small aggregates such as micelles or as large droplets up to a few microns in size. Thus, the lipophilic microphase-forming material is not completely water soluble. The lipophilic microphase-forming material also is capable of forming a plurality of small lipophilic microphases in an in vivo aqueous use environment without the need for stirring, agitation or other mechanical energy. The material need not be self-emulsifying. Nevertheless, preferably the lipophilic microphase-forming material should not agglomerate into a single phase within the use environment, but should remain as a plurality of microphases for at least 1 hour and preferably longer. When the composition is administered to an in vitro aqueous use environment, the lipophilic microphase-forming material should form a plurality of microphases with at most only slight agitation of the use environment. The microphases remain small for at least 1 hour, and more preferably at least 4 hours, after administration to the use environment.

It should be noted that some lipophilic materials that do not form a plurality of microphases when administered alone may often form such phases when administered with the polymer/drug solid amorphous dispersions. This is particularly true when the lipophilic microphase-forming material is dispersed, along with the drug and the polymer in the solid amorphous dispersion.

The resulting lipophilic microphases formed in the aqueous use environment are small. By "small" is meant that the lipophilic microphase-forming material forms lipophilic microphases that are generally less than about 10 µm in characteristic diameter. By "characteristic diameter" is meant the volume average diameter of the microphase in the use environment. The characteristic diameter may be determined by standard measurement techniques, such as dynamic light scattering and static light scattering, or by examination via optical- or scanning-election microscopy, transmission-electron microscopy, coulter-counting methods, and size-exclusion field-flow fractionation. The resulting particles may be smaller, such as less than 1 µm in characteristic diameter, less than 100 nm in characteristic diameter, and less than 50 nm in characteristic diameter. The size of the microphases depends on the other components of the composition, such as the drug and polymer, the manner in which the components of the composition are combined, (such as having the lipophilic microphase-forming material dispersed within the polymer/drug dispersion), as well as the components of the use environment. This is particularly true in an in vivo use environment where the presence of proteins, bile salts, and other surface active agents may cause some compositions to form suitably small lipophilic microphases even though they do not form such microphases in in vitro tests. In addition, it is well known that, in the in vivo environment, many lipophilic microphase-forming materials such as mono-, di-, and tri-glycerides may undergo chemical conversion to other species that in time form the microphases. Thus the ultimate test of an appropriate lipophilic microphase-forming material and composition is best conducted in the in vivo use environment.

The lability of a drug from the free drug phase into and out of the lipophilic microphase is generally a function of the microphase size. By "lability" is meant the kinetics or rate of drug release or drug partitioning into or out of the microphase. Generally, for a given mass of lipophilic microphase-forming material, lability increases as the size of the microphase decreases. As the solubility of the drug decreases, it is preferable for the characteristic size of the microphase to be smaller. Thus, when the solubility of the drug is extremely low, such as about 1 µg/ml or less, preferred compositions generally form microphases less than about 1 µm in characteristic diameter when dosed to the in vivo use environment.

The drug should also have a relatively high partition coefficient in the lipophilic microphase-forming material. By partition coefficient is meant the ratio of the concentration of drug present in the lipophilic microphases to the free drug concentration as follows:

$$K_p = \frac{[Drug]_{lipophile}}{[Drug]_{free}} \quad (1)$$

where $K_p$ is the partition coefficient, $[Drug]_{lipophile}$ is the concentration of the drug in the lipophilic microphases, and $[Drug]_{free}$ is the free drug concentration.

In a given volume of the aqueous use environment, the total amount of drug in the lipophilic microphases is also dependent on the amount of lipophilic microphase present. Thus the concentration of drug in the lipophilic microphase per unit volume of the aqueous use environment, $[Drug]_{aqueous,lipophile}$, is given by:

$$[Drug]_{aqueous,lipophile} = X_{lipophile} \cdot K_p \cdot [Drug]_{free}$$

where $X_{lipophile}$ is the volume fraction of the lipophilic microphase in the use environment.

In situations where the drug is only present as free drug and drug within the lipophilic microphase, the total dissolved drug concentration $[Drug]_{aqueous,total}$ is given by:

$$[D]_{aqueous,total} = [Drug]_{free} + [Drug]_{aqueous,lipophile}$$

$$[Drug]_{aqueous,total} = [Drug]_{free} \cdot [1 + X_{lipophile} \cdot K_p] \quad (II)$$

In order for the presence of the lipophile to have a large impact on the bioavailability of a composition, there generally must be a significant fraction of the total drug dosed that is within the lipophilic microphase. By significant fraction it is generally meant that at least about 0.1% and preferably at least about 1% of the total drug dosed is present in the use environment within the lipophilic microphase-forming material. According to the above equations, the fraction of the total drug present within the lipophilic microphases generally increases with: (1) increasing $K_p$, (2) increasing $X_{lipophile}$, (3) increasing $[Drug]_{free}$.

Since there are practical limits to the size of oral dosage forms that may be administered, it is generally undesirable to have large values of $X_{lipophile}$. For example, when the compositions of the present invention are formed into an oral tablet or capsule for administration, the mass of the tablet or capsule is generally less than about 1000 mg and preferably less than about 700 mg. Since a significant portion of the dosage form must also comprise the active drug and other excipients, the maximum amount of lipophilic microphase-forming material in a single oral dosage form is about 500 mg. When dosed orally to the GI tract of a human, the aqueous volume into which the lipophilic microphase-forming material composition disperses is generally about 50 ml up to about 500 ml, depending on the fed state of the subject. Thus, the maximum practical value for $X_{lipophile}$ is about 0.001 to 0.01. Thus, for example, when the dose of the drug is 100 mg, it is desirable to have at least 0.1 wt % (0.1 mg) and preferably at least 1 wt % (1 mg) of the drug be present in the lipophilic microphase-forming material. This generally means that the concentration of drug in the lipophilic microphase-forming material (in wt %) when the composition is dosed orally to a human is at least about 0.1 mg/500 mg or 0.02 wt % and preferably at least about 0.2 wt % (1 mg/500 mg).

The minimum $K_p$ may be determined by determining the $K_p$ necessary to achieve the desired concentration of drug in the lipophilic microphase forming material. Since the concentration of drug in the lipophilic microphase-forming material at equilibrium is given by:

$$[Drug]_{lipophile} = [Drug]_{free} \cdot K_P$$

then the minimum $K_p$ may be determined by setting the free drug concentration, $[Drug]_{free}$, to the maximum aqueous solubility of the drug, $S_{xtal}$. The minimum $K_p$ should generally be at least about 0.02 wt %/$S_{xtal}$, preferably greater than about 0.2 wt %/$S_{xtal}$, more preferably greater than about 0.5 wt %/$S_{xtal}$, even more preferably greater than about 1 wt %/$S_{xtal}$, and most preferably greater than about 2 wt %/$S_{xtal}$. (The maximum aqueous solubility, $S_{xtal}$, is the maximum solubility of the thermodynamically most stable crystalline form of the drug, or the undispersed amorphous form if the crystalline form is unknown, over the physiologically pH range of 1-8.) Thus, when the maximum aqueous solubility of the drug is about 100 μg/ml or about 0.01 wt %, then $K_p$ should be greater than about 2 (0.02 wt %/0.01 wt %), preferably greater than about 20 (0.2 wt %/0.01 wt %), more preferably greater than about 50 (0.5 wt %/0.01 wt %), even more preferably greater than 100 (1 wt %/0.01 wt %), and most preferably greater than 200 (2 wt %/0.01 wt %). Thus, the minimum and preferred minimum values for $K_p$ for various drug solubilities are given as follows:

| $S_{xtal}$ (μg/ml)[wt %] | Minimum $K_p$ | Preferred Minimum $K_p$ | More Preferred Minimum $K_p$ | Even More Preferred Minimum $K_p$ | Most Preferred Minimum $K_p$ |
|---|---|---|---|---|---|
| 100 [0.01] | 2 | 20 | 50 | 100 | 200 |
| 10 [0.001] | 20 | 200 | 500 | 1,000 | 2,000 |
| 1.0 [1 × 10$^{-4}$] | 200 | 2,000 | 5,000 | 10,000 | 20,000 |
| 0.1 [1 × 10$^{-5}$] | 2,000 | 20,000 | 50,000 | 100,000 | 200,000 |
| 0.01 [1 × 10$^{-6}$] | 20,000 | 200,000 | 500,000 | 1,000,000 | 2,000,000 |

The partition coefficient $K_p$ for a drug in a particular lipophilic microphase-forming material may be determined by any method or series of experiments in which the concentration of drug present as free drug and drug present in lipophilic microphases can be determined. One exemplary method is as follows. Crystalline drug (or amorphous drug if the crystalline form of the drug is not known) is added to an appropriate buffer solution such as PBS (described below) at an amount such that if all of the drug dissolved the concentration would be greater than the equilibrium solubility of the drug. The concentration of free drug in the solution is then determined by any technique that can quantitatively measure the amount of dissolved drug in solution, such as high-performance liquid chromatography (HPLC) or nuclear magnetic resonance (NMR) spectroscopy. Typically, this is accomplished by collecting a sample of the solution containing the drug and either filtering or centrifuging the sample to remove undissolved drug species, and then analyzing the concentration of the remaining dissolved drug. This technique provides the value of $[Drug]_{free}$ in Equation I. Next, crystalline drug is added to an appropriate buffer solution to which various amounts of the lipophilic microphase-forming material had been added, such as 1 vol %, 2 vol % and 3 vol %, again at an amount such that if all of the drug dissolved the concentration of drug either present as free drug or in the lipophilic microphase would be greater than the equilibrium solubility of the drug with the lipophilic microphase-forming material present. The total concentration of total dissolved drug, that is the sum of drug present as free drug plus drug present in lipophilic microphases, (as given in Equation II)—is determined using the same techniques described above. The total dissolved drug concentration $[Drug]_{aqueous,total}$ is then plotted versus the vol % lipophilic microphase-forming material in the solution. The slope of the line for this graph is equal to the product of the free drug concentration (which is normally assumed to be equal to the solubility of the drug in the absence of the lipophilic microphase-forming material, or $S_{xtal}$) and $K_p$. Thus, $K_p$=slope/$S_{xtal}$. When the aqueous solubility of the lipophilic microphase-forming material or the "critical micelle concentration" (CMC) of the lipophilic microphase-forming material is very small relative to the amount of lipophilic microphase-forming material used in the above experiment, the y-intercept of the line through the data points is approximately equal to the crystalline drug solubility, $S_{xtal}$. When the amount of lipophilic microphase-forming material used is only slightly larger than the CMC or the lipophilic microphase-forming material aqueous solubility, then the values of $X_{lipophile}$ should be corrected by subtracting the CMC or solubility from the total volume fraction of lipophilic microphase-forming material added to the solution.

In a preferred embodiment of this invention, the lipophilic microphase-forming material is part of the solid amorphous dispersion of drug and polymer. In such cases, it is preferred that the dispersion comprise no greater than 50 wt % lipophilic microphase-forming material, preferably no greater than 40 wt %, more preferably no greater than 30 wt %. When the lipophilic microphase-forming material is included in the dispersion, the glass-transition temperature ($T_g$) of the dispersion may be reduced if the melting point of the lipophilic microphase-forming material is low, potentially leading to reduced stability of the drug in the dispersion. However, in many cases the addition of the lipophilic microphase-forming material also increases the solubility of the drug in the polymer plus lipophilic microphase-forming material matrix. As a result its addition may improve the stability of the dispersion regardless of its effect on $T_g$. In cases where it is necessary to keep the $T_g$ of the dispersion high and the lipophilic microphase-forming material is part of the dispersion, it is generally preferable for the material, if crystalline, to have a relatively high melting point and if amorphous to have a relatively high $T_g$. Thus, the melt temperature or $T_g$ of the lipophilic microphase-forming material should be sufficiently high such that the $T_g$ of the dispersion is at least 50° C. when tested under ambient humidity conditions (e.g., 50% relative humidity). More preferably, the $T_g$ of the dispersion is at least 70° C. at 50% relative humidity, and most preferably at least 100° C. at 50% relative humidity. Other factors, such as the $T_g$ of the drug, the $T_g$ of the concentration-enhancing polymer, the drug:polymer ratio, and the amount of lipophilic microphase-forming material included in the dispersion may affect the $T_g$ of the dispersion, and these factors should be considered when selecting a lipophilic microphase-forming material to use in a composition.

Another preferred embodiment of the present invention is a solid oral dosage form comprising the novel compositions. The solid dosage form may take the form of one or more tablets or capsules or a multiplicity of particles or granules. When the solid dosage form is one or more tablets or capsules, the dosage form may be taken orally by swallowing whole, chewed and then swallowed, or the dosage form may disintegrate and optionally dissolve in the mouth and then be swallowed. When the solid dosage form is a multiplicity of small particles or granules the powder or granules may be ingested by any known method, including first dispersing in an aqueous vehicle and then swallowing, or mixing with food and then ingesting along with the food.

In order for the compositions of the present invention to be efficiently formed into solid dosage forms it is generally desirable for the lipophilic microphase-forming materials to have relatively high melting points and relatively high $T_g$ values. However, even lipophilic microphase-forming materials that are liquid at room temperature may be formed into solid dosage forms as long as the amount incorporated into the dosage form is not too high.

When the lipophilic microphase-forming material is either a liquid at room temperature or becomes liquid at a temperature of about 50° C. or less, a preferred embodiment is to disperse the lipophilic microphase-forming material in a solid excipient. The lipophilic microphase-forming material may be adsorbed to the surface of a solid material such as microcrystalline cellulose; silica; dibasic calcium phosphate; calcium silicate (Zeodor™); clays, such as kaolin (hydrated aluminum silicate), bentonite (hydrated aluminum silicate), hectorite and Veegum®; Na-, Al-, and Fe-montmorillonite; silicon dioxide (Cab-O—Sil® or Aerosil®); magnesium trisilicate; aluminum hydroxide; magnesium hydroxide, magnesium oxide or talc. Highly porous materials such as calcium silicate are preferred. This embodiment has the advantage of separating the lipophilic microphase-forming material from the solid amorphous dispersion, thus minimizing the effect of the lipophilic microphase-forming material on the glass transition temperature of the dispersion. As described in more detail below, it is desired that the dispersion have a high glass transition temperature in order to provide good physical stability.

Alternatively, it may be dispersed in a water soluble or water dispersible polymer, as either a separate phase, or homogeneously throughout the polymer. In one preferred embodiment, the lipophilic microphase-forming material is dispersed in a concentration-enhancing polymer. Such lipophilic microphase-forming material dispersions serve to (1) render the lipophilic microphase-forming material solid to aid in incorporation into solid dosage forms, (2) aid in dispersing of the lipophilic microphase-forming material as a microphase, and (3) provide additional concentration-enhancing polymer for generating and sustaining high concentrations of dissolved drug. In an often particularly preferred embodiment, the lipophilic microphase-forming material is dispersed, along with the drug, in one or more concentration enhancing polymers to form a single dispersion comprising the drug, the one or more concentration-enhancing polymers, and the lipophilic microphase-forming material. Such lipophilic microphase-forming material dispersions are often preferred even when the lipophilic microphase-forming material is a solid below about 50° C.

The lipophilic microphase-forming material may be either hydrophobic, amphiphilic, or a mixture of a hydrophobic and an amphiphilic material. By "amphiphilic" material is meant a material that has both hydrophobic and hydrophilic portions. Since hydrophobic materials alone tend not to form small microphases in an aqueous use environment, amphiphilic and mixtures of amphiphilic and hydrophobic materials are preferred. However, it is known that some such hydrophobic materials will form microphases due to the influence of (1) other excipients such as the concentration-enhancing polymer, (2) the drug itself, or (3) naturally occurring components of the GI tract. Thus, hydrophobic materials alone form a part of the invention as long as they form suitably small microphases when the compositions or dosage forms are administered to a use environment. The use of a mixture of hydrophobic and amphiphilic material may be preferred because the hydrophobic material often provides a higher partition coefficient, while the amphiphilic material may limit or reduce the size of the lipophilic microphases in the use environment. Thus, such mixtures may have higher lability and higher partition coefficients.

Generally, the lipophilic microphase-forming materials have a molecular weight of less than about 20,000 daltons. However, most lipophilic microphase-forming materials have molecular weights below about 2,000 daltons. Additionally, the lipophilic microphase-forming materials are water immiscible and form lipophilic microphases. The lipophilic microphase-forming material is therefore distinct from the concentration-enhancing polymer. The concentration-enhancing polymers generally have molecular weights of greater than about 10,000 daltons, are more soluble or dispersible in the use environment, and are generally less hydrophobic.

Examples of amphiphilic materials suitable for use as the lipophilic microphase-forming material include: sulfonated hydrocarbons and their salts, such as sodium 1,4-bis(2-ethylhexyl)sulfosuccinate, also known as docusate sodium (CROPOL) and sodium lauryl sulfate (SLS); poloxamers, also referred to as polyoxyethylene-polyoxypropylene block copolymers (PLURONICs, LUTROLs); polyoxyethylene alkyl ethers (CREMOPHOR A, BRIJ); polyoxyethylene sorbitan fatty acid esters (polysorbates, TWEEN); short-chain glyceryl mono-alkylates (HODAG, IMWITTOR, MYRJ); polyglycolized glycerides (GELUCIREs); mono- and di-alkylate esters of polyols, such as glycerol; nonionic surfactants such as polyoxyethylene 20 sorbitan monooleate, (polysorbate 80, sold under the trademark TWEEN 80, available commercially from ICI); polyoxyethylene 20 sorbitan monolaurate (Polysorbate 20, TWEEN 20); polyethylene (40 or 60) hydrogenated castor oil (available under the trademarks CREMOPHOR® RH40 and RH60 from BASF); polyoxyethylene (35) castor oil (CREMOPHOR® EL); polyethylene (60) hydrogenated castor oil (Nikkol HCO-60); alpha tocopheryl polyethylene glycol 1000 succinate (Vitamin E TPGS); glyceryl PEG 8 caprylate/caprate (available commercially under the registered trademark LABRASOL® from Gattefosse); PEG 32 glyceryl laurate (sold commercially under the registered trademark GELUCIRE 44/14 by Gattefosse), polyoxyethylene fatty acid esters (available commercially under the registered trademark MYRJ from ICI), polyoxyethylene fatty acid ethers (available commercially under the registered trademark BRIJ from ICI). Alkylate esters of polyols may be considered amphiphilic or hydrophobic depending on the number of alkylates per molecule and the number of carbons in the alkylate. When the polyol is glycerol, mono- and di-alkylates are often considered amphiphilic while trialkylates of glycerol are generally considered hydrophobic. However, some scientists classify even medium chain mono- and di-glycerides as hydrophobic. See for example Patel et al U.S. Pat. No. 6,294,192 (B1), which is incorporated herein in its entirety by reference. Regardless of the classification, compositions comprising mono- and di-glycerides are preferred compositions of this invention. Other suitable amphiphilic materials may be found in Patel, U.S. Pat. No. 6,294,192 and are listed as "hydrophobic non-ionic surfactants and hydrophilic ionic surfactants."

It should be noted that some amphiphilic materials may not be water immiscible by themselves, but instead are at least somewhat water soluble. Such amphiphilic materials may nevertheless be used in mixtures to form the lipophilic microphase, particularly when used as mixtures with hydrophobic materials.

Examples of hydrophobic materials suitable for use as the lipophilic microphase-forming material include: medium-chain glyceryl mono-, di-, and tri-alkylates (CAPMUL MCM, MIGLYOL 810, MYVEROL 18-92, ARLACEL 186, fractionated coconut oil, light vegetable oils); sorbitan esters (ARLACEL 20, ARLACEL 40); long-chain fatty alcohols (stearyl alcohol, cetyl alcohol, cetostearyl alcohol); long-chain fatty-acids (stearic acid); and phospholipids (egg lecithin, soybean lecithin, vegetable lecithin, sodium taurocholic acid, and 1,2-diacyl-sn-glycero-3-phosphocholine, such as 1-palm itoyl-2-oleyl-sn-glycero-3-phosphocoline, 1,2-dipalm itoyl-sn-glycero-3-phosphocholine, 1,2-distearoyl-sn-glycero-3-phosphocholine, 1-plamitoyl-2-stearoyl-sn-glycero-3-phosphocholine, and other natural or synthetic phosphatidyl cholines); mono and diglycerides of capric and caprylic acid under the following registered trademarks: Capmul® MCM, MCM 8, and MCM 10, available commercially from Abitec, and Imwitor® 988, 742 or 308, available commercially from Condea Vista; polyoxyethylene 6 apricot kernel oil, available under the registered trademark Labrafil® M 1944 CS from Gattefosse; polyoxyethylene corn oil, available commercially as Labrafil® M 2125; propylene glycol monolaurate, available commercially as Lauroglycol from Gattefosse; propylene glycol dicaprylate/caprate available commercially as Captex® 200 from Abitec or Miglyol® 840 from Condea Vista, polyglyceryl oleate available commercially as Plurol oleique from Gattefosse, sorbitan esters of fatty acids (e.g., Span® 20, Crill® 1, Crill® 4, available commercially from ICI and Croda), and glyceryl monooleate (Maisine, Peceol); medium chain triglycerides (MCT, C6-C12) and long chain triglycerides (LCT, C14-C20) and mixtures of mono-, di-, and triglycerides, or lipophilic derivatives of fatty acids such as esters with alkyl alcohols; fractionated coconut oils, such as Miglyol® 812 which is a 56% caprylic (C8) and 36% capric (C10) triglyceride, Miglyol® 810 (68% C8 and 28% C10), Neobee® M5, Captex® 300, Captex® 355, and Crodamol® GTCC; (Miglyols are supplied by Condea Vista Inc. (Huls), Neobee® by Stepan Europe, Voreppe, France, Captex by Abitec Corp., and Crodamol by Croda Corp); vegetable oils such as soybean, safflower, corn, olive, cottonseed, arachis, sunflowerseed, palm, or rapeseed; fatty acid esters of alkyl alcohols such as ethyl oleate and glyceryl monooleate. Other hydrophobic materials suitable for use as the lipophilic microphase-forming material include those listed in Patel, U.S. Pat. No. 6,294,192 as "hydrophobic surfactants." Exemplary classes of hydrophobic materials include: fatty alcohols; polyoxyethylene alkylethers; fatty acids; glycerol fatty acid monoesters; glycerol fatty acid diesters; acetylated glycerol fatty acid monoesters; acetylated glycerol fatty acid diesters, lower alcohol fatty acid esters; polyethylene glycol fatty acid esters; polyethylene glycol glycerol fatty acid esters; polypropylene glycol fatty acid esters; polyoxyethylene glycerides; lactic acid derivatives of monoglycerides; lactic acid derivatives of diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof. Mixtures of relatively hydrophilic materials, such as those termed herein as "amphiphilic" or in Patel as "hydrophilic surfactants" and the above hydrophobic materials are particularly suitable. Specifically, the mixtures of hydrophobic surfactants and hydrophilic surfactants disclosed by Patel are suitable and for many compositions, preferred. However, unlike Patel, mixtures that include triglycerides as a hydrophobic component are also suitable.

In one embodiment, the lipophilic microphase-forming material is selected from the group consisting of polyglycolized glycerides (GELUCIREs); polyethylene (40 or 60) hydrogenated castor oil (available under the trademarks CREMOPHOR® RH40 and RH60 from BASF); polyoxyethylene (35) castor oil (CREMOPHOR® EL); polyethylene (60) hydrogenated castor oil (Nikkol HCO-60); alpha tocopheryl polyethylene glycol 1000 succinate (Vitamin E TPGS); glyceryl PEG 8 caprylate/caprate (available commercially under the registered trademark LABRASOL® from Gattefosse); PEG 32 glyceryl laurate (sold commercially under the registered trademark GELUCIRE 44/14 by Gattefosse); polyoxyethylene fatty acid esters (available commercially under the registered trademark MYRJ from ICI); polyoxyethylene fatty acid ethers (available commercially under the registered trademark BRIJ from ICI); poly-oxyethylene-polyoxypropylene block copolymers (PLURONICs, LUTROLs); polyoxyethylene alkyl ethers (CREMOPHOR A, BRIJ); long-chain fatty alcohols (stearyl alcohol, cetyl alcohol, cetostearyl alcohol); long-chain fatty-acids (stearic acid); polyoxyethylene 6 apricot kernel oil, available under the registered trademark Labrafil® M 1944 CS from Gattefosse; polyoxyethylene corn oil, available commercially as Labrafil® M 2125; propylene glycol monolaurate, available commercially as Lauroglycol from Gattefosse; polyglyceryl oleate available commercially as Plurol oleique from Gattefosse; triglycerides, including medium chain triglycerides (MCT, $C_6$-$C_{12}$) and long chain triglycerides (LCT, $C_{14}$-$C_{20}$); fractionated coconut oils, such as Miglyol® 812 which is a 56% caprylic ($C_8$) and 36% capric ($C_{10}$) triglyceride, Miglyol® 810 (68% $C_8$ and 28% $C_{10}$), Neobee® M5, Captex® 300, Captex® 355, and Crodamol® GTCC; (Miglyols are supplied by Condea Vista Inc. [Huls], Neobee® by Stepan Europe, Voreppe, France, Captex by Abitec Corp., and Crodamol by Croda Corp); vegetable oils such as soybean, safflower, corn, olive, cottonseed, arachis, sunflowerseed, palm, or rapeseed; polyoxyethylene alkylethers; fatty acids; lower alcohol fatty acid esters; polyethylene glycol fatty acid esters; polyethylene glycol glycerol fatty acid esters; polypropylene glycol fatty acid esters; polyoxyethylene glycerides; lactic acid derivatives of monoglycerides; lactic acid derivatives of diglycerides; propylene glycol diglycerides; transesterified vegetable oils; sterols; sterol derivatives; sugar esters; sugar ethers; sucroglycerides; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; and mixtures thereof.

Especially preferred lipophilic microphase-forming materials include mixtures of polyethoxylated castor oils and medium-chain glyceryl mono-, di-, and/or tri-alkylates, (such as mixtures of CREMOPHOR RH40 and CAPMUL MCM), mixtures of polyoxyethylene sorbitan fatty acid esters and medium-chain glyceryl mono-, di-, and/or tri-alkylates, (such as mixtures of TWEEN 80 and CAPMUL MCM), mixtures of polyethoxylated castor oils and medium-chain glyceryl mono-, di-, and/or tri-alkylates, (such as mixtures of CREMOPHOR RH40 and ARLACEL 20), mixtures of sodium taurocholic acid and palmitoyl-2-oleyl-sn-glycero-3-phosphocholine and other natural or synthetic phosphatidylcholines, and mixtures of polyglycolized glycerides and medium-chain glyceryl mono-, di-, and/or tri-alkylates, (such as mixtures of Gelucire 44/14 and CAPMUL MCM).

The lipophilic microphase-forming material is present in a sufficient amount so that the combination of the solid amorphous dispersion and lipophilic microphase-forming material provides concentration enhancement, as described more fully below. In general, the lipophilic microphase-forming material is either present in the composition or co-administered with the solid amorphous dispersion such that the weight ratio of the lipophilic microphase-forming material to drug (hereinafter referred to as the lipophile:drug ratio) ranges from 0.1 to 100 (wt/wt), and more typically from 0.2 to 50.

The optimum amount of the lipophilic microphase-forming material depends on the mass of the dose of the drug, the partition coefficient, and the solubility of the drug. The optimum mass of the lipophilic microphase-forming material increases as the mass of the dose increases. The optimum mass of the lipophilic microphase-forming material decreases as the partition coefficient increases and as the solubility increases.

Nevertheless, in general, the amount of lipophilic microphase forming material present in the composition should not be so high that the concentration of free drug obtained in the use environment is much lower than that obtained when less lipophilic microphase-forming material is combined with the solid amorphous dispersion and is introduced to the use environment. Generally, when the amount of lipophilic microphase-forming material that is added to the composition is greater than the amount such that all of the drug introduced to the use environment is either present as free drug or is in the lipophilic microphases, then the performance, in terms of improving drug absorption, will be reduced relative to lower levels of the lipophilic microphase-forming material. Thus, it is preferred for compositions to contain less than this "maximum preferred level." Nonetheless, levels of lipophilic microphase-forming material somewhat above this level may still improve drug absorption relative to the dispersion alone. This maximum preferred level will depend on the free drug concentration ($[Drug]_{free}$, typically given in mg/ml), the density of the lipophilic microphase-forming material ($\rho_{lipophile}$, typically given in mg/ml), and the partition coefficient ($K_p$). The maximum preferred lipophile:drug ratio is given by the following equation:

$$\text{Maximum lipophile:drug ratio} = \rho_{lipophile}/(K_p \cdot [Drug]_{free})$$

It should be noted that for some values of $K_p$ and $[Drug]_{free}$, the maximum preferred lipophile:drug ratio will be quite large. For example, when $\rho_{lipophile}=1000$ mg/mL, $K_p=100$, and $[Drug]_{free}=0.001$ mg/mL, the maximum preferred lipophile:drug ratio is calculated to be 10,000. If the drug dose is, for example 100 mg, this results in a maximum preferred lipophile dose of 1000 g. Such high doses of lipophile are impractical. Thus when the value of $K_p$ and/or $[Drug]_{free}$ are low, the maximum preferred lipophile:drug ratio may be limited by practical considerations such as the maximum dose well tolerated by the subject or the maximum practical size of the dosage form.

Preparation of Compositions

Compositions of the present invention may be prepared according to any technique that results in a mixture comprising (1) a solid amorphous dispersion comprising a low-solubility drug and a concentration-enhancing polymer and (2) a lipophilic microphase-forming material. In one method, a solid amorphous dispersion of the drug, polymer and lipophilic microphase-forming material is formed so that the lipophilic microphase-forming material is included in the dispersion itself. Alternatively, a solid amorphous dispersion of drug and polymer may be formed and then mixed with the lipophilic microphase-forming material so that the lipophilic microphase-forming material is mixed with but not included within the dispersion. As yet another alternative, the solid amorphous dispersion of the drug and polymer may be prepared and then co-administered with a lipophilic microphase-forming material to a use environment, so that the dispersion and lipophilic microphase-forming material are both present in the use environment.

Dispersions of a low-solubility drug and polymer may be made according to any known process which results in at least a "major portion" (meaning at least 60 wt %) of the drug being in the amorphous state. While the drug in its pure state may be crystalline or amorphous, at least a major portion of the drug in the dispersion is amorphous. By "amorphous" is meant simply that the drug is in a non-crystalline state. As used herein, the term "a major portion" of the drug means that at least 60 wt % of the drug in the dispersion is in the amorphous form. It has also been found that the aqueous concentration of the drug in a use environment tends to improve as the fraction of drug present in the amorphous state in the dispersion increases. Accordingly the drug in the dispersion may be substantially amorphous, and preferably may be almost completely amorphous. As used herein, "substantially amorphous" means that at least 75 wt % of the drug is amorphous and "almost completely amorphous" means that at least 90 wt % of the drug is amorphous. The amount of drug in the dispersion which is amorphous or crystalline may be measured by powder X-ray diffraction, Scanning Electron Microscope (SEM) analysis, differential scanning calorimetry (DSC), or any other standard quantitative measurement.

The amorphous drug can exist as a pure phase, as a solid solution of drug homogeneously distributed throughout the polymer or any combination of these states or those states that lie intermediate between them. The dispersion is preferably "substantially homogeneous" so that the amorphous drug is dispersed as homogeneously as possible throughout the polymer. Dispersions of the present invention that are substantially homogeneous generally have improved concentration-enhancing properties and, in turn improved bioavailability, relative to nonhomogeneous dispersions. As used herein, "substantially homogeneous" means that the drug present in relatively pure amorphous domains within the solid dispersion is relatively small, on the order of less than 20%, and preferably less than 10% of the total amount of drug.

While the dispersion may have some drug-rich domains, it is preferred that the dispersion itself have a single glass transition temperature ($T_g$) which demonstrates that the dispersion is substantially homogeneous. This contrasts with a simple physical mixture of pure amorphous drug particles and pure amorphous polymer particles which generally displays two distinct $T_g$s, one that of the drug and one that of the polymer. $T_g$ as used herein is the characteristic temperature where a glassy material, upon gradual heating, undergoes a relatively rapid (e.g., 10 to 100 seconds) physical change from a glass state to a rubber state. Dispersions with more than one $T_g$, indicating at least partial amorphous phase separation, may also function well, particularly when neither amorphous phase is comprised only of amorphous drug, but rather also contains a significant amount of concentration-enhancing polymer.

When the lipophilic microphase-forming material is included in the dispersion, it may exist as a pure lipophilic phase, as a solid solution of the lipophilic microphase-forming material homogeneously distributed throughout the dispersion, or any combination of these states or those states that lie intermediate between them. Generally, it is preferred that the lipophilic microphase-forming material be well distributed throughout the dispersion, either as small, preferably less than 1 μm in diameter, relatively pure domains of lipophilic microphase-forming material, or more preferably, dispersed such that it is at least partially dissolved in the drug and polymer solid amorphous dispersion.

The solid amorphous dispersions of the drug and polymer may be made according to any conventional process for forming dispersions. When the lipophilic microphase-forming material is included in the dispersion, such dispersions may also be made according to any conventional process for forming dispersions. Such processes include mechanical, thermal and solvent processes. Exemplary mechanical processes include milling and extrusion; melt processes include high temperature fusion, solvent modified fusion and melt-congeal processes; and solvent processes include non-solvent precipitation, spray coating and spray-drying. See, for example, U.S. Pat. No. 5,456,923 and U.S. Pat. No. 5,939,099 which describe formation of dispersions via extrusion processes; U.S. Pat. No. 5,340,591 and U.S. Pat. No. 4,673,564 which describe forming dispersions by milling processes; and U.S. Pat. No. 5,707,646 and U.S. Pat. No. 4,894,235 which describe the formation of dispersions via melt/congeal processes, the disclosures of which are incorporated by reference.

In one embodiment, the solid amorphous dispersion of drug and concentration-enhancing polymer may be formed via a melt-congeal or melt-extrusion process. Such processes are particularly suitable when the drug has a relatively low melting point, typically less than about 200° C. and preferably less than about 150° C. In such processes, a molten mixture comprising the drug and concentration-enhancing polymer, and optionally, lipophilic microphase-forming material, is rapidly cooled such that the molten mixture solidifies to form a solid amorphous dispersion. By "molten mixture" is meant that the mixture comprising the drug and concentration-enhancing polymer is about 10° C. or more above the melting point of the lowest melting point component in the composition. The drug may exist in the molten mixture as a pure phase, as a solution of drug homogeneously distributed throughout the molten mixture, or any combination of these states or those states that lie intermediate between them. The molten mixture is preferably substantially homogeneous so that the drug is dispersed as homogeneously as possible throughout the molten mixture. As mentioned above, it is also desirable that the lipophilic microphase-forming material be dispersed as homogeneously as possible throughout the molten mixture. When the temperature of the molten mixture is below the melting point of both the drug and the concentration-enhancing polymer, the molten excipients, concentration-enhancing polymer, and drug are preferably sufficiently soluble in each other that a substantial portion of the drug disperses in the concentration-enhancing polymer or excipients. It is often preferred that the mixture be heated above the lower of the melting point of the concentration-enhancing polymer, the drug, and the lipophilic microphase-forming material, if present.

Generally, the processing temperature may vary from 50° C. up to about 200° C. or higher, depending on the melting point of the drug and polymer, which is a function of the polymer grade selected, and the lipophilic microphase-forming material, if present. However, the processing temperature should not be so high that an unacceptably high level of degradation of the drug or polymer occurs. In some cases, the molten mixture should be formed under an inert atmosphere to prevent degradation of the drug and/or polymer at the processing temperature. When relatively high temperatures are used, it is often preferable to minimize the time that the mixture is at the elevated temperature to minimize degradation.

The molten mixture may also comprise an excipient that will reduce the melting temperature of the composition (either the drug and/or the polymer), allowing processing at lower temperature. When such excipients have low volatility and substantially remain in the mixture upon solidification, they generally can comprise up to 30 wt % of the molten mixture. For example, a plasticizer may be added to the composition to reduce the melting temperature of the polymer. Examples of plasticizers include water, triethylcitrate, triacetin, and dibutyl sebacate. Volatile agents that dissolve or swell the polymer, such as acetone, water, methanol, and ethyl acetate, may also be added in low quantities to reduce the melting point of the composition. When such volatile excipients are added, at least a portion, up to essentially all of such excipients, may evaporate in the process of or following conversion of the molten mixture to a solid mixture. In such cases, the processing may be considered to be a combination of solvent processing and melt-congealing or melt-extrusion. Removal of such volatile excipients from the molten mixture can be accomplished by breaking up or atomizing the molten mixture into small droplets and contacting the droplets with a fluid such that the droplets both cool and lose all or part of the volatile excipient. Examples of other excipients that can be added to the composition to reduce the processing temperature include low molecular weight polymers or oligomers, such as polyethylene glycol, polyvinylpyrrolidone, and poloxamers; fats and oils, including mono-, di-, and triglycerides; natural and synthetic waxes, such as carnauba wax, beeswax, microcrystalline wax, castor wax, and paraffin wax; long-chain alcohols, such as cetyl alcohol and stearyl alcohol; and long-chain fatty acids, such as stearic acid. When the lipophilic microphase-forming material is added to the molten mixture, the lipophilic microphase-forming material may act to reduce the melting temperature of the composition. As mentioned above, when the excipient added is volatile, it may be removed from the mixture while still molten or following solidification to form the solid amorphous dispersion.

Virtually any process may be used to form the molten mixture. One method involves melting the concentration-enhancing polymer in a vessel and then adding the drug, and optionally, the lipophilic microphase-forming material, to the molten polymer. Another method involves melting the drug, and optionally, the lipophilic microphase-forming material, in a vessel and then adding the concentration-enhancing polymer. As the lipophilic microphase-forming material may often be a liquid at room temperature or may have a low melting point relative to the polymer, it is often preferred to use this last method. In yet another method, a solid blend of the drug, concentration-enhancing polymer, and optionally, the lipophilic microphase-forming material, may be added to a vessel and the blend heated to form the molten mixture. When the lipophilic microphase-forming material is included in the dispersion, it may be mixed with the drug and polymer before or after forming the molten mixture. Alternatively, the lipophilic microphase-forming material may first be melted, if it is not already liquid, and the drug and polymer added to the molten lipophilic microphase-forming material to form the molten mixture.

Once the molten mixture is formed, it may be mixed to ensure the drug is homogeneously distributed throughout the molten mixture. Such mixing may be done using mechanical means, such as overhead mixers, magnetically driven mixers and stir bars, planetary mixers, and homogenizers. Optionally, when the molten mixture is formed in a vessel, the contents of the vessel can be pumped out of the vessel and through an in-line or static mixer and then returned to the vessel. The amount of shear used to mix the molten mixture should be sufficiently high to ensure uniform distribution of the drug in the molten mixture. The molten mixture can be mixed from a few minutes to several hours, the mixing time being dependent on the viscosity of the mixture and the solubility of the drug and any optional excipients in the concentration-enhancing polymer.

An alternative method of preparing the molten mixture is to use two vessels, melting the drug and optionally, the lipophilic microphase-forming material in the first vessel and the concentration-enhancing polymer and optionally, lipophilic microphase-forming material in a second vessel. The two melts are then pumped through an in-line static mixer or extruder to produce the molten mixture that is then rapidly solidified.

Alternatively, the molten mixture can be generated using an extruder, such as a single-screw or twin-screw extruder, both well known in the art. In such devices, a solid, or semi-solid mixture of the composition is fed to the extruder whereby the combination of heat and shear forces within the extruder produce a uniformly mixed molten mixture, which can then be rapidly solidified to form the solid amorphous dispersion. The solid feed can be prepared using methods well known in the art for obtaining solid mixtures with high content uniformity. Alternatively, the extruder may be equipped with two or more feeders, allowing the drug, and optionally the lipophilic microphase-forming material, to be fed to the extruder through one feeder and the polymer, and optionally the lipophilic microphase-forming material, through the other. Other excipients to reduce the processing temperature as described above may be included in the solid feed, or in the case of liquid excipients, such as water, may be injected into the extruder using methods well-known in the art.

The extruder should be designed such that it produces a molten mixture with the drug uniformly distributed throughout the composition. The various zones in the extruder should be heated to appropriate temperatures to obtain the desired extrudate temperature as well as the desired degree of mixing or shear, using procedures well known in the art.

When the drug has a high solubility in the concentration-enhancing polymer, and optionally the lipophilic microphase-forming material, a lower amount of mechanical energy will be required to form the dispersion. In such cases, when the melting point of the undispersed drug is greater than the melting point of the undispersed concentration-enhancing polymer, and optionally the lipophilic microphase-forming material, the processing temperature may be below the melting temperature of the undispersed drug but greater than the melting point of the polymer, and optionally the lipophilic microphase-forming material, since the drug will dissolve into the molten polymer, and if present, the lipophilic microphase-forming material. When the melting point of the undispersed drug is less than the melting point of the undispersed concentration-enhancing polymer, and optionally the lipophilic microphase-forming material, the processing temperature may be above the melting point of the undispersed drug but below the melting point of the undispersed concentration-enhancing polymer since the molten drug will dissolve in the polymer, and optionally the lipophilic microphase-forming material, or be absorbed into the polymer.

When the drug has a low solubility in the polymer and optional lipophilic microphase-forming material, a higher amount of mechanical energy may be required to form the dispersion. Here, the processing temperature may need to be above the melting point of the drug and the polymer. As mentioned above, alternatively, a liquid or low-melting point excipient may be added that promotes melting or the mutual solubility of the concentration-enhancing polymer and the drug. A high amount of mechanical energy may be needed to mix the drug and the polymer to form a dispersion. Typically, the lowest processing temperature and an extruder design that imparts the lowest amount of mechanical energy (e.g., shear) that produces a satisfactory dispersion (substantially amorphous and substantially homogeneous) is chosen in order to minimize the exposure of the drug to harsh conditions.

Once the molten mixture of drug, concentration-enhancing polymer, and optionally the lipophilic microphase-forming material is formed, the mixture should be rapidly solidified to form the solid amorphous dispersion. Rapid solidification is only necessary when the drug and other materials in the molten mixture are not miscible. By "rapidly solidified" is meant that the molten mixture is solidified sufficiently fast such that substantial phase separation of the drug from the other materials does not occur. Typically, this means that the mixture should be solidified in less than about 10 minutes, preferably less than about 5 minutes, more preferably less than about 1 minute. If the mixture is not rapidly solidified, phase separation can occur, if the materials are not miscible at storage temperatures, resulting in the formation of drug-rich phases. Solidification often takes place primarily by cooling the molten mixture to at least about 10° C. and preferably at least about 30° C. below its melting point. As mentioned above, solidification can be additionally promoted by evaporation of all or part of one or more volatile excipients or solvents. To promote rapid cooling and evaporation of volatile excipients, the molten mixture is often formed into a high surface area shape such as a rod or fiber or droplets. For example, the molten mixture can be forced through one or more small holes to form long thin fibers or rods or may be fed to a device, such as an atomizer such as a rotating disk, that breaks the molten mixture up into droplets from 1 μm to 1 cm in diameter. The droplets are then contacted with a relatively cool fluid such as air or nitrogen to promote cooling and evaporation.

Another method for forming solid amorphous dispersions is by "solvent processing," which consists of dissolution of the drug and one or more concentration-enhancing polymers, as well as, optionally, the one or more materials that make up the lipophilic microphase-forming material, in a common solvent. Optionally, the lipophilic microphase-forming material may also be dissolved or suspended in the solvent. "Common" here means that the solvent, which can be a mixture of compounds, will dissolve the drug and the polymer(s). Although it need not completely dissolve the lipophilic microphase-forming material, it is often preferred to use a solvent in which the lipophilic microphase-forming material is also soluble. After both the drug, the polymer, and optionally the lipophilic microphase-forming material have been dissolved, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent.

The solvent may be removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, a portion of the heat required for evaporation of solvent may be provided by heating the spray solution.

Solvents suitable for spray-drying can be any compound in which the drug and polymer are mutually soluble. If the lipophilic microphase-forming material is part of the dispersion, it may be soluble in the solvent or may be suspended in the solvent. Preferably, the solvent is volatile with a boiling point of 150° C. or less. In addition, the solvent should have relatively low toxicity and be removed from the dispersion to a level that is acceptable according to The International Committee on Harmonization (ICH) guidelines. Removal of solvent to this level may require a processing step such as tray-drying subsequent to the spray-drying or spray-coating process. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water as long as the polymer and drug are sufficiently soluble to make the spray-drying process practicable.

Generally, the temperature and flow rate of the drying gas is chosen so that the polymer/drug-solution droplets are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 µm to 500 µm in diameter, with 5 µm to 100 µm being more typical. The large surface-to-volume ratio of the droplets and the large driving force for evaporation of solvent leads to actual drying times of a few seconds or less, and more typically less than 0.1 second. Solidification times should be less than 100 seconds, preferably less than a few seconds, and more preferably less than 1 second. The size of droplets formed during the spray-drying process are typically less than about 200 µm in diameter. The resultant solid particles thus formed are generally less than about 200 µm in diameter.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of the drug molecules in the dispersion, thereby improving its stability. Generally, the solvent content of the dispersion as it leaves the spray-drying chamber should be less than 10 wt % and preferably less than 2 wt %. In some cases, it may be preferable to spray a solvent or a solution of a polymer or other excipient into the spray-drying chamber to form granules, so long as the dispersion is not adversely affected.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem. Eng. Prog. Monogr. Series* 2 (1954). Further details of the spray drying procedure are disclosed in commonly owned Provisional U.S. Patent Application Ser. Nos. 60/354,080 and 60/353,986, the disclosures of which are incorporated herein by reference.

The amount of polymer relative to the amount of drug present in the solid amorphous dispersion depends on the drug and polymer and may vary widely from a drug-to-polymer weight ratio of from 0.01 to about 4 (e.g., 1 wt % drug to 80 wt % drug in the absence of other excipients in the dispersion). However, in most cases it is preferred that the drug-to-polymer ratio is greater than about 0.05 (4.8 wt % drug in the absence of other excipients) and less than about 2.5 (71 wt % drug in the absence of other excipients). In some embodiments, the addition of the lipophilic microphase-forming material allows for higher drug loadings. Thus, the drug:polymer ratio may be at least 1.

The dispersion is usually in the form of small particles. The particles may be less than 500 µm in diameter, less than 100 µm in diameter, less than 50 µm in diameter, or less than 25 µm in diameter. When the dispersion is formed by spray-drying, the resulting dispersion is in the form of such small particles. When the dispersion is formed by other methods such by melt-congeal or melt-extrusion processes, the resulting dispersion may be sieved, ground, milled, or otherwise processed to yield a plurality of small particles.

In cases where the composition of the present invention is prepared by mixing the previously formed solid amorphous dispersion with the lipophilic microphase-forming material, the mixture can be prepared by any method that results in a uniform mixture of the dispersion and the lipophilic microphase-forming material. Mixing processes include physical mixing as well as wet- and dry-granulation and coating processes. The resulting mixture may be a solid composition comprising the dispersion suspended in the lipophilic microphase-forming material, a mixture of separate dispersion particles and lipophilic microphase-forming material particles interspersed with one another, a series of respective layers of dispersion and lipophilic microphase-forming material, or any other mixture of dispersion and lipophilic microphase-forming material.

In many cases, to aid the dispersing of the lipophilic microphase-forming material in the use environment, it is often desirable to disperse the lipophilic microphase-forming material in a water soluble or water dispersable matrix prior to forming the mixture. Alternatively, the lipophilic microphase-forming material may be adsorbed to a water insoluble substrate such as dibasic calcium phosphate, calcium carbonate, microcrystalline cellulose, silicon dioxide calcium silicate; clays, such as kaolin (hydrated aluminum silicate), bentonite (hydrated aluminum silicate), hectorite and Veegum®; silicon dioxide (Cab-O—Sil® or Aerosil®); magnesium trisilicate; aluminum hydroxide; magnesium hydroxide, magnesium oxide or talc. Highly porous materials such as calcium silicate are preferred. When the lipophilic microphase-forming material is dispersed in a water dispersable matrix, the dispersion may be formed by any of the processes described previously for forming the polymer/drug dispersion including melt processes such as extrusion, solvent processes such as spray-drying, as well as conventional wet and dry granulation processes. Following forming the adsorbate dispersion or granule of lipophilic microphase-forming material the dispersion or granule containing the lipophilic microphase-forming material may then be blended with the polymer/drug dispersion.

When it is desired to adsorb (or absorb) the lipophilic microphase-forming material onto a solid substrate, the lipophilic microphase-forming material may be adsorbed onto the solid substrate using any conventional method. In one exemplary method, the substrate is initially dried to remove water. The lipophilic microphase-forming material is then combined with the substrate. The lipophilic microphase-forming material may be combined with the substrate by the use of a planetary mixer, a Z-blade mixer, a rotogranulator or similar equipment. Preferably, the amount of lipophilic microphase-forming material is kept sufficiently low so that the mixture of lipophilic microphase-forming material and solid substrate forms a free-flowing powder. The proportion of lipophilic microphase-forming material to solid substrate preferably is less than about 4:1 (wt:wt) lipophilic microphase-forming material to solid substrate. As the weight ratio of lipophilic microphase-forming material to substrate increases, the material becomes cake-like, and then oily or slurry-like. The particular ratio will depend on the porosity of the substrate and the nature of the lipophilic microphase-forming material. The lipophilic microphase-forming material may be diluted in a solvent such as methanol prior to adsorbing the lipophilic microphase-forming material to the solid substrate. The resulting slurry is dried, for example in a vacuum desiccator, to form a solid material comprising the lipophilic microphase-forming material and substrate. This solid material may then be combined with the solid amorphous dispersion.

Mixing methods include convective mixing, shear mixing, or diffusive mixing. Convective mixing involves moving a relatively large mass of material from one part of a powder bed to another, by means of blades or paddles, revolving screw, or an inversion of the powder bed. Shear mixing occurs when slip planes are formed in the material to be mixed. Diffusive mixing involves an exchange of position by single particles. These mixing processes can be performed using equipment in batch or continuous mode. Tumbling mixers (e.g., twin-shell) are commonly used equipment for batch processing. Continuous mixing can be used to improve composition uniformity. Continuous mixers include "in-line" mixers and extruders. Extruders may be single screw or twin-screw. Twin-screw extruders may turn in the same or opposite direction.

Milling may also be employed to combine the dispersion and the lipophilic microphase-forming material. Milling is the mechanical process of reducing the particle size of solids (comminution). Because in some cases milling may alter crystalline structure and cause chemical changes for some materials, milling conditions are generally chosen which do not alter the physical form of the dispersion in the sense that the drug in the dispersion is no longer amorphous. The most common types of milling equipment are the rotary cutter, the hammer, the roller, and fluid energy mills.

Equipment choice depends on the characteristics of the ingredients in the composition (e.g., soft, abrasive, or friable). Wet- or dry-milling techniques can be chosen for several of these processes, also depending on the characteristics of the ingredients (e.g. dispersion stability in solvent). The milling process may serve simultaneously as a mixing process if the feed materials are heterogeneous. Conventional mixing and milling processes suitable for use in the present invention are discussed more fully in Lachman, et al., *The Theory and Practice of Industrial Pharmacy* (3d Ed. 1986).

The dispersion and lipophilic microphase-forming material may also be combined by dry- or wet-granulating processes as long as granulating conditions are chosen such that the dispersion remains a solid amorphous dispersion. In addition to the physical mixtures described above, the compositions of the present invention may constitute any device or collection of devices that accomplishes the objective of delivering to the use environment both the dispersion and the lipophilic microphase-forming material.

In a particularly preferred embodiment, the polymer/drug dispersion in lipophilic microphase-forming material, or alternatively, a solid amorphous dispersion of polymer, drug and lipophilic microphase-forming material, are incorporated into the same solid dosage form such as a capsule or tablet. In order to deliver the desired dose of drug to the use environment, more than one such capsule or tablet may be dosed. A solid amorphous dispersion of drug and polymer, together with the lipophilic microphase-forming material, may both be delivered "immediately" to the use environment, meaning that both are substantially released from the dosage form in less than about 30 minutes, or one or both of the dispersion and lipophilic microphase-forming material may be delivered over a period of 1 to 20 hours in a sustained, delayed or pulsatile fashion. Thus, the dosage form may be considered a controlled release dosage form in which the dispersion, the lipophilic microphase-forming material or both the dispersion and the lipophilic microphase-forming material are delivered to the use environment over a 1- to 20-hour period.

Thus, in the case of oral administration to an animal, the dosage form may constitute a layered tablet wherein one or more layers comprise the dispersion and one or more other layers comprise the lipophilic microphase-forming material. Alternatively, the dosage form may be a coated tablet wherein the tablet core comprises the dispersion and the coating comprises the lipophilic microphase-forming material or wherein the tablet core comprises the lipophilic microphase-forming material and the coating comprises the dispersion (which may be formed during the coating process). In addition, the dispersion and the lipophilic microphase-forming material may even be present in different dosage forms such as tablets or beads and may be administered simultaneously or separately as long as both the dispersion and lipophilic microphase-forming material are administered in such a way that the dispersion and lipophilic microphase-forming material are both present in the use environment. In yet another specific embodiment, the polymer/drug dispersion may be dissolved or suspended in an aqueous vehicle containing the lipophilic microphase-forming material and the aqueous suspension subsequently dosed to the use environment.

Concentration-Enhancement

The compositions of the present invention provide concentration-enhancement in a use environment relative to one or more control compositions. The compositions of the present invention may provide concentration-enhancement relative to a first control composition consisting essentially of the solid amorphous dispersion of the drug and polymer but without any lipophilic microphase forming material present. Thus, the lipophilic microphase forming material is either present in the composition or co-administered in a sufficient amount to provide concentration enhancement (as described more fully below) relative to a first control consisting essentially of an equivalent amount of the solid amorphous dispersion of drug and concentration-enhancing polymer but with no lipophilic microphase forming material present. That is, the first control composition is identical to the composition comprising the solid amorphous dispersion and the lipophilic microphase-forming material except for the absence of the lipophilic microphase-forming material.

Alternatively, the compositions of the present invention provide concentration enhancement relative to a second control composition consisting essentially of the same lipophilic microphase-forming material combined with undispersed crystalline drug in an amount equivalent to the amount of drug in the dispersion of the test composition, but with no concentration-enhancing polymer present. Thus, the second control composition is identical to the composition of the invention except that (1) the drug is in the form of undispersed crystalline drug rather than dispersed in the concentration-enhancing polymer and (2) there is no concentration-enhancing polymer present. In cases where more than one crystal form of the drug is known, the control composition consists of the crystalline form that is most thermodynamically stable at ambient conditions (25° C. and 50% relative humidity). In cases where no crystalline form of the drug is known, undispersed amorphous drug may be substituted for crystalline drug.

At a minimum, compositions of the present invention provide concentration enhancement in a use environment relative to at least one of the two above controls. Preferably, compositions of the present invention will provide concentration enhancement in a use environment relative to both of the above two controls.

Compositions comprising an amorphous dispersion and lipophilic microphase-forming material provide concentration-enhancement in either an in vivo or in vitro use environment. In an in vivo use environment, the concentration-enhancement may result in either enhanced relative bioavailability and/or a more regular fed/fasted bioavailability ratio (that is, a fed/fasted bioavailability ratio closer to 1). In an in vitro use environment, concentration enhancement may be either enhanced drug concentration in highly mobile drug species, reduced precipitate, enhanced maximum drug concentration, or enhanced dissolution area under the concentration versus time curve (AUC).

As used herein, a "use environment" can be either the in vivo environment of the GI tract, subdermal, intranasal, buccal, intrathecal, ocular, intraaurial, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS). Concentration enhancement may be determined through either in vivo tests or through in vitro dissolution tests. A composition of the present invention meets the concentration enhancement criteria in at least one of the above test environments.

In one aspect, the compositions comprising an amorphous dispersion and lipophilic microphase-forming material provide improved relative bioavailability relative to either the first control composition, the second control composition, or preferably both. Relative bioavailability may be tested in vivo in animals or humans using conventional methods for making such a determination. An in vivo test, such as a crossover study, may be used to determine whether a test composition provides an enhanced relative bioavailability compared with one or both control compositions. It is to be understood by those skilled in the art that such in vivo tests are conventionally carried out under fasted conditions. In an in vivo crossover study a "test composition" of dispersion and lipophilic microphase-forming material is dosed to half a group of test subjects and, after an appropriate washout period (e.g., one week) the same subjects are dosed with a control composition. As described above, the control composition may be either the first control composition which consists of the amorphous dispersion with no lipophilic microphase-forming material present, or the second control composition, which consists of an equivalent amount of the drug in undispersed crystalline form and an equivalent amount of the lipophilic microphase-forming material but with no concentration-enhancing polymer present. The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis).

To demonstrate improved bioavailability relative to the first control composition and the second control composition, a "three-way in vivo crossover" study may be conducted where the three compositions are the test composition, the first control composition and the second composition.

A preferred embodiment is one in which the relative bioavailability of the test composition is at least 1.25 relative to either the first control composition or the second control composition. (That is, the AUC in the blood provided by the test composition is at least 1.25-fold the AUC provided by the control composition.) The relative bioavailability may be at least 2.0, and more preferably at least 3.0, relative to either control composition. The determination of AUCs is a well-known procedure and is described, for example, in Welling, "Pharmacokinetics Processes and Mathematics," ACS Monograph 185 (1986). An even more preferred embodiment of the present invention is one for which the relative bioavailability of the test composition is at least 1.25-fold relative to both the first control composition and the second control composition.

Alternatively, in another separate aspect, the compositions comprising an amorphous dispersion and lipophilic microphase-forming material provide more regular absorption. In this aspect, the compositions provide a fed/fasted bioavailability ratio that is near 1.0. By "fed/fasted bioavailability ratio" is meant the AUC in the blood provided by a composition dosed to a subject in the fed state, divided by the AUC in the blood provided by the same composition dosed to a subject in the fasted state. By "subject in the fed state" is meant a subject who has eaten a Food and Drug Administration (FDA)-recommended standard high fat breakfast within a period of twenty minutes, and then ingested (i.e., swallowed) the test dosage form essentially immediately thereafter. A standard high-fat breakfast consists of, for example, two eggs fried in one tablespoon of butter, two strips of bacon, six ounces of hash brown potatoes, two pieces of toast with two teaspoons of butter and two pats of jelly, and eight ounces of whole milk. This standard high-fat breakfast contains approximately 964 calories, 54% supplied as fat (58 gm) and 12% supplied as protein, calculated using the monograph "Nutritive Value of Foods", U.S. Department of Agriculture Home and Garden Bulletin Number 72. Additional food can also be consumed within the twenty-minute period and the subject still qualifies as "fed". A "subject in the fasted state" for purposes of definition is one who has not eaten for at least eight hours, typically overnight, prior to ingestion of the dosage form.

Thus, a preferred composition of the present invention comprising a dispersion and a lipophilic microphase forming material provides a fed/fasted bioavailability ratio of from 0.5 to 2.0. Preferably, the compositions provide a fed/fasted bioavailability ratio of from 0.67 to 1.5, and more preferably of from 0.8 to 1.25. Preferably, the composition of the present invention provides a fed/fasted bioavailability ratio that is closer to 1 than at least one of the first control compositions and the second composition, more preferably both compositions.

Alternatively, the concentration-enhancement provided by the compositions of the present invention may be determined in in vitro dissolution tests in an appropriate use environment. It has been determined that enhanced drug concentration in in vitro dissolution tests in PBS solution is a good indicator of in vivo performance and bioavailability. By "PBS solution" is meant an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. In particular, a composition of the present invention may be dissolution-tested by adding it to PBS solution and agitating to promote dissolution. A composition of the invention is one which meets the criteria set out below when dosed to PBS solution.

In one aspect, the compositions comprising a dispersion and a lipophilic microphase forming material, following introduction to an aqueous use environment, provide a concentration of "highly mobile" drug that is at least 2-fold the concentration of highly mobile drug provided by either the first control composition or the second control composition. Preferably, the concentration of highly mobile drug provided by the composition is at least 3-fold, more preferably at least 4-fold the concentration of highly mobile drug provided by either the first control composition or the second control composition. Preferred embodiments meet these criteria with both the first control composition and the second control composition.

By "highly mobile" is meant drug that is present either as free drug or in a lipophilic microphase. Drug that is highly mobile may be quantified using analytical techniques capable of measuring the concentration of drug in solution that is not in the form of polymer/drug assemblies or in precipitate. For example, a nuclear magnetic resonance (NMR) technique may be used, since the NMR measurement only yields a well-resolved signal for species that are sufficiently small or mobile that they may rapidly rotate. In particular, the NMR signal has been found to be proportional to the amount of highly mobile drug; that is, free drug and any drug that may be present in a mobile, solvated non-aggregated state such as in lipophilic microphases but not drug present in large polymer/drug assemblies. Highly mobile drug may also be quantified through permeation analysis in which the rate of drug transport through a dialysis or other suitable membrane is proportional to the free drug concentration.

Alternatively, the compositions comprising a dispersion and a lipophilic microphase forming material provide concentration enhancement by reducing the mass of precipitate formed in the use environment relative to the control composition. Reducing the mass of precipitate results in an increase in the amount of drug present in drug forms that are more labile and mobile, resulting in an increase in relative bioavailability. As used herein, the "precipitate ratio" is defined as the mass of drug present in the precipitate obtained when a first control composition (e.g., the solid amorphous dispersion alone) is administered to an aqueous use environment divided by the mass of drug present in the precipitate obtained when a test composition comprising the solid amorphous dispersion and lipophilic microphase-forming material is administered to an equivalent amount of the same use environment. Thus, if 30 mg of drug is present in the precipitate formed when a control composition is administered to a test medium and 20 mg of drug is present in the precipitate formed when a test composition is administered to the same test medium, the precipitate ratio is equal to 1.5 (30/20). The compositions comprising a dispersion and a lipophilic microphase forming material, following introduction to an aqueous environment of use, provide a precipitate ratio that is at least 1.25 relative to the first control composition previously described. Preferably, the composition of the present invention provides a precipitate ratio that is at least 2-fold, more preferably at least 3-fold relative to the control composition.

The amount of drug present in precipitate may be determined by any analytical technique that can quantitatively make such a determination. In one method, the amount of drug present in precipitate is determined by subtracting the total dissolved drug concentration from the theoretical concentration of drug if all of the drug added to the test medium had dissolved. As used herein, the term "total dissolved drug" refers to the total amount of drug dissolved in the aqueous solution, and includes drug present in the form of free drug, micelles, lipophilic microphases and polymer/drug assemblies. Specifically, this means that total dissolved drug may be determined by separating out any undissolved drug by centrifugation or filtration and then measuring the amount of drug remaining in the supernatant or filtrate. Total dissolved drug is typically taken as that material that either passes a 0.45 μm syringe filter or, alternatively, the material that remains in the supernatant following centrifugation. Filtration can be conducted using a 13 mm, 0.45 μm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (>10-40%) than that obtained with the filter specified above but will still allow identification of preferred compositions.

Alternatively, drug in precipitate may be determined by collecting the solids obtained upon centrifugation or filtration of the aqueous solution, dissolution of the solids in an appropriate solvent, such as methanol, dimethylsulfoxide, or dimethylacetamide, and then analyzing for the drug using any quantitative analytical technique such as HPLC or NMR.

In another alternative aspect, the composition comprising a solid amorphous dispersion and a lipophilic microphase forming material may provide a Maximum total dissolved Drug Concentration (MDC) that is at least 1.25-fold the MDC of either the first control composition or the second control composition. In other words, if the MDC provided by either control composition is 100 µg/mL, then a composition comprising a dispersion and lipophilic microphase-forming material provides an MDC of at least 125 µg/mL. More preferably, the MDC of drug achieved with the compositions of the present invention are at least 2-fold, and even more preferably at least 3-fold, that of either control composition. To facilitate testing, the maximum drug concentration may be taken as the maximum concentration achieved within 90 to 180 minutes following administration of the drug. Preferred compositions meet these criteria for both the first control composition and the second control composition.

Alternatively, the compositions comprising a dispersion and a lipophilic microphase-forming material may provide in an aqueous use environment a total dissolved drug concentration versus time Area Under The Curve (AUC), for any period of at least 90 minutes between the time of introduction into the use environment and about 270 minutes following introduction to the use environment that is at least 1.25-fold that of either the first control composition or the second control composition. More preferably, the AUC achieved with the compositions of the present invention are at least 2-fold and more preferably at least 3-fold that of either control composition. Preferred compositions meet these criteria for both the first control composition and the second control composition.

In a particularly preferred embodiment of the present invention, the inventors have found that certain compositions provide a surprisingly "synergistic enhancement" in the various concentration and bioavailability criteria described above. The "synergistic enhancement" is determined by comparing the performance of the test composition of solid amorphous dispersion and lipophilic microphase-forming material to a "third control composition." The third control composition consists essentially of the undispersed drug alone in its thermodynamically lowest energy state, typically the most stable crystalline form or its amorphous form if a crystalline form is unknown. Preferred compositions of solid amorphous dispersions of drug and polymer and lipophilic microphase-forming material exhibit synergistic enhancement by performing better than would be expected by simply adding the enhancement provided by a dispersion with the enhancement provided by the lipophilic microphase-forming material.

To determine synergy, it is necessary to determine the performance of the first control composition, the second control composition, and the third control composition either in in vivo or in in vitro dissolution tests. The relative enhancement of the first control composition (e.g., the solid amorphous dispersion but with no lipophilic microphase-forming material) is determined with respect to the third control composition. For example, if the first control composition provides an $AUC_{90}$ (that is, the AUC obtained during the first 90 minutes following introduction of the composition to a use environment) of 20,000 min*µg/ml and the third control composition provides an $AUC_{90}$ of 1,000 min*µg/ml, the first control composition has a relative enhancement of 20-fold.

Likewise, the relative enhancement of the second control composition (e.g., the undispersed crystalline drug with lipophilic microphase-forming material but no concentration-enhancing polymer) is determined with respect to the third control composition. For example, if the second control composition provides an $AUC_{90}$ of 40,000 min*µg/ml and the third control composition provides an $AUC_{90}$ of 1,000 min*µg/ml, the second control composition has a relative enhancement of 40-fold.

Compositions of the present invention provide synergistic enhancement when the relative enhancement provided by the test composition compared with the third control composition is greater than the sum of the relative enhancement provided by the first control composition and the relative enhancement provided by second control composition. Returning to the examples described above, if the first control composition provided a relative enhancement of 20-fold, and the second control composition provided a relative enhancement of 40-fold, the sum of their relative enhancements would be 60-fold. Thus, a test composition provides synergistic enhancement when it provides a relative enhancement of greater than 60-fold compared with the third control composition.

The synergistic enhancement may also be determined by comparing the relative bioavailability of the test composition, first control composition, and second control composition relative to the third control composition. Synergistic enhancement would be shown where the relative bioavailability of the test composition is greater than the sum of the relative bioavailability of the first control composition and the relative bioavailability of the second control composition. For example, if the first control composition provides a relative bioavailability of 1.5 with respect to the third control composition, and the second control composition provides a relative bioavailability of 2.0 with respect to the third control composition, the test composition shows synergistic enhancement when it has a relative bioavailability relative to the third control composition greater than 3.5.

In particular, the inventors have noted that synergistic enhancements in concentration are often obtained by compositions in which the lipophilic microphase-forming material is dispersed, along with the drug, in the concentration-enhancing polymer. Such compositions are highly preferred.

Low-Solubility Drugs

The drug is a "low-solubility drug," meaning that the drug may be either "substantially water-insoluble," which means that the drug has a minimum aqueous solubility at physiologically relevant pH (e.g., pH 1-8) of less than 0.01 mg/mL, "sparingly water-soluble," that is, has an aqueous solubility up to about 1 to 2 mg/mL, or even low to moderate aqueous-solubility, having an aqueous-solubility from about 1 mg/mL to as high as about 20 to 40 mg/mL. In general, it may be said that the drug has a dose-to-aqueous solubility ratio greater than 10 mL, and more typically greater than 100 mL, where the drug solubility (mg/mL) is the minimum value observed in any physiologically relevant aqueous solution (e.g., those with pH values between 1 and 8) including USP simulated gastric and intestinal buffers, and dose is in mg. The dose-to-aqueous-solubility-ratio may be determined by simply dividing the dose (in mg) by the aqueous solubility (in mg/mL).

The use of the lipophilic microphase-forming material works particularly well for very low solubility drugs. Thus, the invention finds particular utility where the drug has a solubility of less than 100 µg/ml, and even greater utility where the solubility is less than 10 µg/ml.

In addition, the invention finds utility when the drug has a relatively high absorption rate constant. By "absorption rate constant" is meant a constant that describes the rate at which the drug is moved from the site of administration (e.g., the GI tract of an animal) to the extra-cellular compartment of the body. Absorption rate constants are generally described by zero-order or first-order models. See for example, Remington's *The Science and Practice of Pharmacy*, 20$^{th}$ Ed (2000). The invention finds particular utility when the drug has an absorption rate constant of at least 0.005 min$^{-1}$, more utility when the drug has an absorption rate constant of at least 0.01 min$^{-1}$, and even more utility when the drug has an absorption rate constant of at least 0.03 min$^{-1}$ or higher.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents, glycogen phosphorylase inhibitors, and cholesterol ester transfer protein inhibitors.

Each named drug should be understood to include the neutral form of the drug, pharmaceutically acceptable salts, as well as prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)—N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethylphenoxy)-pyridin-4-yl]-(1-ethylpropyl)-amine, 3,5-dimethyl-4-(3'-pentoxy)-2-(2',4',6'-trimethylphenoxy)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril, and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein inhibitors include [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]-4-[3,5-bis-trifluoromethyl-benzyl)-methoxycarbonyl-amino]-2-ethyl-6-trifluoromethyl-3,4-dihydro-2H-quinoline-1-carboxylic acid ethyl ester, and [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester.

Concentration-Enhancing Polymers

The composition also includes a concentration-enhancing polymer. By "concentration-enhancing" is meant a polymer present in a sufficient amount so that the dispersion provides, at a minimum, either improved AUC, maximum drug concentration, or relative bioavailability relative to a control consisting of an equivalent amount of crystalline drug but with no concentration-enhancing polymer. (Concentration enhancement may be evaluated as described above, except that the dispersion would be the test composition and crystalline drug without any polymer present would be the control composition). Concentration-enhancing polymers should be pharmaceutically acceptable, and should have at least some solubility in aqueous solution at physiologically relevant pHs (e.g., 1-8). Almost any neutral or ionizable polymer that has an aqueous-solubility of at least 0.1 mg/mL over at least a portion of the pH range of 18 may be suitable.

It is preferred that the concentration-enhancing polymer be "amphiphilic" in nature, meaning that the polymer has hydrophobic and hydrophilic portions. Amphiphilic polymers are preferred because it is believed that such polymers tend to have relatively strong interactions with the drug and may promote the formation of various types of polymer/drug assemblies in solution.

A particularly preferred class of amphiphilic polymers are those that are ionizable, the ionizable portions of such polymers, when ionized, constituting at least a portion of the hydrophilic portions of the polymer. For example, while not wishing to be bound by a particular theory, such polymer/drug assemblies may comprise hydrophobic drug clusters surrounded by the concentration-enhancing polymer with the polymer's hydrophobic regions turned inward towards the drug and the hydrophilic regions of the polymer turned outward toward the aqueous environment. Alternatively, depending on the specific chemical nature of the drug, the ionized functional groups of the polymer may associate, for example, via ion pairing or hydrogen bonds, with ionic or polar groups of the drug. In the case of ionizable polymers, the hydrophilic regions of the polymer would include the ionized functional groups. In addition, the repulsion of the like charges of the ionized groups of such polymers (where the polymer is ionizable) may serve to limit the size of the polymer/drug assemblies to the nanometer or submicron scale. Such drug/concentration-enhancing polymer assemblies in solution may well resemble charged polymeric micellar-like structures. In any case, regardless of the mechanism of action, the inventors have observed that such amphiphilic polymers, particularly ionizable cellulosic polymers such as those listed below, have been shown to interact with drug so as to maintain a higher concentration of drug in an aqueous use environment.

One class of polymers suitable for use with the present invention comprises non-ionizable (neutral) non-cellulosic polymers. Exemplary polymers include: vinyl polymers and copolymers having at least one substituent selected from the group consisting of hydroxyl, alkylacyloxy, and cyclicamido; polyvinyl alcohols that have at least a portion of their repeat units in the unhydrolyzed (vinyl acetate) form; polyvinyl alcohol polyvinyl acetate copolymers; polyvinyl pyrrolidone; polyoxyethylene-polyoxypropylene copolymers, also known as poloxamers; and polyethylene polyvinyl alcohol copolymers.

A preferred class of neutral non-cellulosic polymers comprises vinyl copolymers of at least one hydrophilic, hydroxyl-containing repeat unit and at least one hydrophobic, alkyl- or aryl-containing repeat unit. Such neutral vinyl copolymers are termed "amphiphilic hydroxyl-functional vinyl copolymers." Amphiphilic hydroxyl-functional vinyl copolymers are believed to provide high concentration enhancements due to the amphiphilicity of these copolymers which provide both sufficient hydrophobic groups to interact with the hydrophobic, low-solubility drugs and also sufficient hydrophilic groups to have sufficient aqueous solubility for good dissolution. The copolymeric structure of the amphiphilic hydroxyl-functional vinyl copolymers also allows their hydrophilicity and hydrophobicity to be adjusted to maximize performance with a specific low-solubility drug.

The preferred copolymers have the general structure:

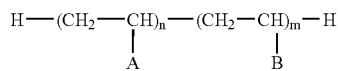

where A and B represent "hydrophilic, hydroxyl-containing" and "hydrophobic" substituents, respectively, and n and m represent the average number of hydrophilic vinyl repeat units and average number of hydrophobic vinyl repeat units respectively per polymer molecule. Copolymers may be block copolymers, random copolymers or they may have structures anywhere between these two extremes. The sum of n and m is generally from about 50 to about 20,000 and therefore the polymers have molecular weights from about 2,500 to about 1,000,000 daltons.

The hydrophilic, hydroxyl-containing repeat units, "A," may simply be hydroxyl (—OH) or it may be any short-chain, 1 to 6 carbon, alkyl with one or more hydroxyls attached thereto. The hydroxyl-substituted alkyl may be attached to the vinyl backbone via carbon-carbon or ether linkages. Thus exemplary "A" structures include, in addition to hydroxyl itself, hydroxymethyl, hydroxyethyl, hydroxypropyl, hydroxymethoxy, hydroxyethoxy and hydroxypropoxy.

The hydrophobic substituent, "B," may simply be: hydrogen (—H), in which case the hydrophobic repeat unit is ethylene; an alkyl or aryl substituent with up to 12 carbons attached via a carbon-carbon bond such as methyl, ethyl or phenyl; an alkyl or aryl substituent with up to 12 carbons attached via an ether linkage such as methoxy, ethoxy or phenoxy; an alkyl or aryl substituent with up to 12 carbons attached via an ester linkage such as acetate, propionate, butyrate or benzoate. The amphiphilic hydroxyl-functional vinyl copolymers of the present invention may be synthesized by any conventional method used to prepare substituted vinyl copolymers. Some substituted vinyl copolymers such as polyvinyl alcohol/polyvinyl acetate are well known and commercially available.

A particularly convenient subclass of amphiphilic hydroxyl-functional vinyl copolymers to synthesize are those where the hydrophobic substituent "B" comprises the hydrophilic substituent "A" to which an alkylate or arylate group is attached via an ester linkage to one or more of the hydroxyls of A. Such copolymers may be synthesized by first forming the homopolymer of the hydrophobic vinyl repeat unit having the substituent B, followed by hydrolysis of a portion of the ester groups to convert a portion of the hydrophobic repeat units to hydrophilic, hydroxyl-containing repeat units having the substituent A. For example, partial hydrolysis of the homopolymer, polyvinylbutyrate, yields the copolymer, vinylalcohol/vinylbutyrate copolymer for which A is hydroxyl (—OH) and B is butyrate (—OOC—$CH_2$—$CH_2$—$CH_3$).

For all types of copolymers, the value of n must be sufficiently large relative to the value of m that the resulting copolymer is at least partially water soluble. Although the value of the ratio, n/m varies depending on the identity of A and B, it is generally at least about 1 and more commonly about 2 or more. The ratio n/m can be as high as 200. When the copolymer is formed by hydrolysis of the hydrophobic homopolymer, the relative values of n and m are typically reported in "percent hydrolysis," which is the fraction (expressed as a percent) of the total repeat units of the copolymer that are in the hydrolyzed or hydroxyl form. The percent hydrolysis, H, is given as $$H = 100 \times \left(\frac{n}{n+m}\right)$$

Thus, vinylbutyrate/vinylalcohol copolymer (formed by hydrolysis of a portion of the butyrate groups) having a percent hydrolysis of 75% has an n/m ratio of 3. A particularly preferred family of amphiphilic hydroxyl-functional vinyl copolymers are those where A is hydroxyl and B is acetate. Such copolymers are termed vinylacetate/vinylalcohol copolymers. Some commercial grades are also sometimes referred to simply as polyvinylalcohol. However, the true homopolymer, polyvinylalcohol is not amphiphilic and is almost entirely water insoluble. Preferred vinylacetate/vinylalcohol copolymers are those where H is between about 67% and 99.5%, or n/m has a value between about 2 and 200. The preferred average molecular weight is between about 2500 and 1,000,000 daltons and more preferably between about 3000 and about 100,000 daltons.

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS manufactured by Rohm Tech Inc., of Malden, Mass.; amine-functionalized polyacrylates and polymethacrylates; proteins such as gelatin and albumin; and carboxylic acid functionalized starches such as starch glycolate. Non-cellulosic polymers that are amphiphilic are copolymers of a relatively hydrophilic and a relatively hydrophobic monomer. Examples include acrylate and methacrylate copolymers. Exemplary commercial grades of such copolymers include the EUDRAGITS, which are copolymers of methacrylates and acrylates.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymers hydroxyl groups. Generally, the degree of substitution of each substituent group can range from 0.05 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulosic polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate.

Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable (neutral) cellulosic polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephtha late, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic substituent may itself be ionizable, such as phthalate or trimellitate substituents.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethyl ethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, hydroxyethyl cellulose acetate succinate and carboxymethyl ethyl cellulose. Of these cellulosic polymers that are at least partially ionized at physiologically relevant pHs, the inventors have found the following to be most preferred: hydroxypropyl methyl cellulose acetate succinate, hydroxypropyl methyl cellulose phthalate, cellulose acetate phthalate, cellulose acetate trimellitate and carboxymethyl ethyl cellulose. The most preferred is hydroxypropyl methyl cellulose acetate succinate.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "neutralized acidic cellulosic polymers" is meant any cellulosic "acidic polymer" for which a significant fraction of the "acidic moieties" or "acidic substituents" have been "neutralized." By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a $pK_a$ of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents." Neutralized acidic polymers are described in more detail in commonly assigned copending provisional patent application U.S. Ser. No. 60/300,256 entitled "Pharmaceutical Compositions of Drugs and Neutralized Acidic Polymers" filed Jun. 22, 2001, the relevant disclosure of which is incorporated by reference.

The glass transition temperature of the dispersion is dependent on the glass transition temperatures of the materials comprising the dispersion. Since one of the primary materials used to form the dispersion is the concentration-enhancing polymer, and since the glass transition temperature of the drug is often relatively low, the concentration-enhancing polymer may be chosen so as to have a relatively high glass transition temperature. Thus, the polymer may have, when equilibrated with humid air having a relative humidity of about 50%, a glass transition temperature of at least 40° C., at least 70° C., or even greater than 100° C.

While specific polymers have been discussed as being suitable for use in the mixtures of the present invention, blends of such polymers may also be suitable. Thus, the term "concentration-enhancing polymer" is intended to include blends of polymers in addition to a single species of polymer.

Excipients and Dosage Forms

Although the key ingredient present in the compositions is simply the mixture of (1) the dispersion of drug and the concentration-enhancing polymer, and (2) the lipophilic microphase-forming material, the inclusion of other excipients in the composition may be useful. These excipients may be utilized in order to formulate the composition into tablets, capsules, suppositories, suspensions, powders for suspension, creams, transdermal patches, depots, and the like. The mixture may be added to other dosage form ingredients in essentially any manner that does not substantially alter the drug. The excipients may be either separate from the mixture and/or included within the mixture.

The addition of pH modifiers such as acids, bases, or buffers may be beneficial, retarding the dissolution of the composition (e.g., acids such as citric acid or succinic acid when the concentration-enhancing polymer is anionic) or, alternatively, enhancing the rate of dissolution of the composition (e.g., bases such as sodium acetate or amines when the polymer is anionic).

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition.

Examples of matrix materials, fillers, or diluents include lactose, mannitol, xylitol, microcrystalline cellulose, dibasic calcium phosphate (dihydrate and anhydrous), and starch.

Examples of disintegrants include sodium starch glycolate, sodium alginate, carboxy methyl cellulose sodium, methyl cellulose, and croscarmellose sodium, and cross-linked forms of polyvinyl pyrrolidone such as those sold under the trade name CROSPOVIDONE (available from BASF Corporation).

Examples of binders include methyl cellulose, microcrystalline cellulose, starch, and gums such as guar gum, and tragacanth.

Examples of lubricants include magnesium stearate, calcium stearate, and stearic acid.

Examples of preservatives include sulfites (an antioxidant), benzalkonium chloride, methyl paraben, propyl paraben, benzyl alcohol and sodium benzoate.

Examples of suspending agents or thickeners include xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, and titanium dioxide.

Examples of anticaking agents or fillers include silicon oxide and lactose.

Examples of solubilizers include ethanol, propylene glycol or polyethylene glycol.

Other conventional excipients may be employed in the compositions of this invention, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

In particular, solid dosage forms such as immediate release tablets, controlled release tablets, delayed release tablets, chewable tablets and analogous capsules containing solid material are a preferred embodiment of this invention. Preferred dosage forms of this type generally comprise from 10 wt % lipophilic microphase-forming material up to 80 wt % lipophilic microphase-forming material as well as the solid amorphous dispersion of drug and concentration-enhancing polymer, together with other optional excipients.

It is conventionally thought that because lipophilic microphase-forming material are typically either low melting point or low $T_g$ solids, or even liquids at room temperature, that they are not considered appropriate additives for such solid dosage forms except at low levels, typically less than about 5 wt % or less to promote wetting and dissolution of the tablet. However, the inventors have found that, contrary to such conventional wisdom, solid dosage forms with excellent properties can be made that have relatively high levels of lipophilic microphase-forming material. In order for such high lipophilic microphase-forming material levels to be utilized in such solid dosage forms, the inventors have found it desirable to adsorb at least a portion of the lipophilic microphase-forming material on a solid substrate or disperse the lipophilic microphase-forming material in a water soluble or water dispersible matrix. As mentioned earlier, appropriate adsorption substrates include materials such as silicon oxide, dibasic calcium phosphate, microcrystalline cellulose, and calcium silicate. Appropriate water soluble or water dispersible dispersion matrix materials include sugars such as sucrose and xylitol, organic acids such as citric acid or lactic acid, water soluble polymers such as polydextrose, polyethylene oxide, or dextrin. Particularly preferred dispersion matrix materials are the concentration-enhancing polymers previously described. In a particularly preferred embodiment, the lipophilic microphase-forming material is dispersed along with drug in the concentration-enhancing polymer. An added advantage of this embodiment, particularly when the lipophilic microphase-forming material is liquid at temperatures below about 50° C., is that relatively high levels of lipophilic microphase-forming material, up to about 50 wt % or in some cases even more, can often be added to the drug/polymer solid amorphous dispersion while still having the resulting material be a solid powder or granule at ambient conditions.

The compositions of the present invention may be delivered by a wide variety of routes, including, but not limited to, oral, nasal, rectal, vaginal, subcutaneous, intravenous, and pulmonary. Generally, the oral route is preferred.

Compositions of this invention may also be used in a wide variety of dosage forms for administration of drugs. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms. In one preferred embodiment, the solid amorphous dispersion of drug and concentration-enhancing polymer is formulated as a dry powder and then, prior to administration, is dispersed in a vehicle that contains the lipophilic microphase-forming material.

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders which are reconstituted by first adding water to one powder to form a solution to which the second powder is combined with agitation to form the suspension.

Generally, it is preferred that the dispersion of drug be formulated for long-term storage in the dry state as this promotes the chemical and physical stability of the drug.

Yet another method to deliver the dispersion and lipophilic microphase-forming material is to co-administer the dispersion and lipophilic microphase-forming material to an in vivo use environment. The solid amorphous dispersion and lipophilic microphase-forming material may each be added separately to the in vivo use environment. Thus, when dosed orally, the dispersion may be taken orally prior to the lipophilic microphase-forming material, at the same time, or after the lipophilic microphase-forming material has been taken orally. In general, if administered separately to an in vivo use environment, the solid amorphous dispersion and the lipophilic microphase-forming material should be administered within 15 minutes of each other.

Since the present invention has an aspect that relates to the treatment of a condition or disorder by treatment with a combination of a polymer/drug solid amorphous dispersion and a lipophilic microphase-forming material which may be co-administered separately, the invention also relates to combining separate pharmaceutical compositions in kit form. The kit comprises two separate pharmaceutical compositions: (1) a composition comprising a solid amorphous dispersion of drug and concentration-enhancing polymer; and (2) a composition comprising a lipophilic microphase-forming material. The amounts of (1) and (2) are such that, when co-administered separately, the condition or disorder is treated and/or remediated. The kit comprises a container for containing the separate compositions such as a divided bottle or a divided foil packet, wherein each compartment contains a plurality of dosage forms (e.g., tablets) comprising (1) or (2). Alternatively, rather than separating the active ingredient-containing dosage forms, the kit may contain separate compartments each of which contains a whole dosage which in turn comprises separate dosage forms. An example of this type of kit is a blister pack wherein each individual blister contains two (or more) tablets, one (or more) tablet(s) comprising pharmaceutical composition (1), and the second (or more) tablet(s) comprising pharmaceutical composition (2). Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician. In the case of the instant invention a kit therefore comprises (1) a therapeutically effective amount of a composition comprising a solid amorphous dispersion of a low-solubility drug and a concentration-enhancing polymer, in a first dosage form;

(2) a therapeutically effective amount of a composition comprising a lipophilic microphase-forming material, in a second dosage form; and (3) a container for containing said first and second dosage forms.

An example of such a kit, alluded to above, is a so-called blister pack. Blister packs are well known in the packaging industry and are widely used for the packaging of pharmaceutical unit dosage forms such as tablets, capsules, and the like. Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. Tablet(s) or capsule(s) can then be removed via said opening.

It may be desirable to provide a memory aid on the kit, e.g., in the form of numbers next to the tablets or capsules whereby the numbers correspond with the days of the regimen during which the tablets or capsules so specified should be ingested. Another example of such a memory aid is a calendar printed on the card, e.g., as follows "First Week, Monday, Tuesday, . . . etc. . . . Second Week, Monday, Tuesday, . . . ", etc. Other variations of memory aids will be readily apparent. A "daily dose" can be a single tablet or capsule or several pills or capsules to be taken on a given day. Also a daily dose of the first compound can consist of one tablet or capsule while a daily dose of the second compound can consist of several tablets or capsules and vice versa. The memory aid should reflect this.

Compositions of the present invention may be used to treat any condition which is subject to treatment by administering a drug.

Other features and embodiments of the invention will become apparent from the following examples which are given for illustration of the invention rather than for limiting its intended scope.

EXAMPLES

Dispersions 1-12

Solid amorphous dispersions of drugs and various concentration-enhancing polymers were prepared by spray-drying each solution of drug and polymer, using either a Niro PSD-1 spray drier or a "mini" spray drier. For Dispersions 1, 2, 9, 10, 11, and 12 the drug was [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester ("Drug 1"). For Dispersions 3 and 4, the drug was the hydrochloride salt form of ziprazidone ("Drug 2A"), while for Dispersion 5, the drug was the free base form of ziprazidone ("Drug 2B"). For Dispersions 6 and 7, the drug was 2-phenanthrenecarboxamide, 4b,5,6,7,8,8a,9,10-octahydro-7-hydroxy-N-[(2-methyl-3-pyridinyl)methyl]-4b-(phenylmethyl)-7-(3,3,3-trifluoropropyl)-, (4bS,7S,8aR) ("Drug 3"). For Dispersion 8, the drug was 5-chloro-1H-indole-2-carboxylic acid [(1S)-benzyl-3-((3R,4S)-dihydroxypyrroldin-1-yl-)-(2R)-hydroxy-3-oxypropyl]amide ("Drug 4").

For Dispersion 1, an amorphous dispersion of Drug 1 and HPMCAS-MF was prepared using a Niro PSD-1 spray drier. First, a spray solution was formed containing 2.5 wt % Drug 1, 7.5 wt % HPMCAS-MF, and 90% acetone. The solution was spray-dried by directing a Niro two-fluid external-mix spray nozzle at 2.7 bar with a feed rate of 190 g/min into the stainless-steel chamber of a Niro PSD-1 spray-dryer, using nitrogen as the drying gas, maintained at a temperature of 137° C. at the inlet; the drying gas and evaporated solvent exited the drier at 49° C.

The resulting solid amorphous dispersion was collected via a cyclone and then dried in a Gruenberg solvent tray-drier by spreading the spray-dried particles onto polyethylene-lined trays to a depth of not more than 1 cm and then drying them at 40° C. for 25 hours. After drying, Dispersion 1 contained 25 wt % Drug 1. The mean diameter of the dispersion particles was 15 m.

Dispersions 2, 3, 8, 10, and 12 were prepared using the same process as described for Dispersion 1, with the exception of the variables noted in Table 1, which summarizes the process conditions. Dispersion 12 was spray-dried using a Niro PSD-4 spray drier and a pressure nozzle (Delvan SDX111 (SA-38)).

TABLE 1

| Disp No. | Drug No. | Drug Mass (g) | Polymer | Polymer Mass (g) | Solvent | Solvent Mass (g) | Nozzle Pressure (bar) | Feed Rate (g/min) | $T_{in}$ (° C.) | $T_{out}$ (° C.) |
|---|---|---|---|---|---|---|---|---|---|---|
| 1 | 1 | 8 | HPMCAS-MF | 24 | Acetone | 288 | 2.7 | 190 | 137 | 49 |
| 2 | 1 | 40 | HPMCAS-MF | 120.4 | Acetone | 840 | 2.7 | 200 | 139 | 50 |
| 3 | 2A | 1 | HPMCAS-HF | 9 | Methanol | 490 | 7.7 | 50 | 120 | 60 |
| 8 | 4 | 150 | HPMCAS-MF | 150 | Acetone | 11,700 | 1.9 | 200 | 180 | 70 |
| 10 | 1 | 4.2 | CMEC | 7.8 | Acetone | 138 | 6.7 | 200 | 110 | 45 |
| 12 | 1 | 144 | HPMCAS-MG | 432 | Acetone | 3024 | 48 | 1667 | 110 | 45 |

For Dispersion 4, an amorphous dispersion of ziprazidone, in the hydrochloride salt form, ("Drug 2A"), was prepared using the mini spray drier. The spray solution consisted of 0.14 wt % Drug 2A, 0.14 wt % HPMCAS-HF, and 99.72 wt % methanol. The solution was pumped into a "mini" spray-drying apparatus via a Cole Parmer 74900 series rate-controlling syringe pump at a rate of 1.3 mL/min. The drug/polymer solution was atomized through a Spraying Systems Co. two-fluid nozzle, Module No. SU1A using a heated stream of nitrogen (100° C.). The spray solution was sprayed into an 11-cm diameter stainless steel chamber. The resulting solid amorphous dispersion was collected on filter paper, dried under vacuum, and stored in a desiccator. After drying, Dispersion 4 contained 50 wt % Drug 2 form A.

Dispersions 5, 6, 7, 9 and 11 were prepared using the same process as described for Dispersion 4, with the exception of the variables noted in Table 2, which summarizes the process conditions. Note that for Dispersion 11 the lipophilic microphase-forming material (Capmul MCM) was included in the solvent solution used to form the dispersion.

TABLE 2

| Disp. No. | Drug No. | Drug Mass (mg) | Polymer | Polymer Mass (mg) | Solvent | Solvent Mass (g) | Feed Rate (mL/min) | $T_{in}$ (° C.) |
|---|---|---|---|---|---|---|---|---|
| 4 | 2A | 500.2 | HPMCAS-HF | 500.2 | Methanol | 356.0 | 1.3 | 100 |
| 5 | 2B | 500.2 | HPMCAS-HF | 500.1 | Methanol | 166.0 | 1.3 | 100 |
| 6 | 3 | 25.4 | CAP | 225.6 | Acetone | 25 | 1.3 | 100 |
| 7 | 3 | 25.3 | HPMCAS-MF | 225.0 | Acetone | 25 | 1.3 | 100 |
| 9 | 1 | 3.0 | HPMC | 27 | MeOH/Acetone 1/1 | 10 | 1.3 | 100 |
| 11 | 1 | 40 | HPMCAS-MF | 120 | Acetone | 12 | 1.0 | 90 |

Table 3 summarizes the various dispersions used in the Examples which follow.

TABLE 3

| Dispersion No. | Drug No. | Drug Conc. in Dispersion (active, wt %) | Polymer | Spray-drier Used to Prepare Dispersion |
|---|---|---|---|---|
| 1 | 1 | 25 | HPMCAS-MF | Niro PSD-1 |
| 2 | 1 | 25 | HPMCAS-MF | Niro PSD-1 |
| 3 | 2A | 10 | HPMCAS-HF | Niro PSD-1 |
| 4 | 2A | 50 | HPMCAS-HF | Mini |
| 5 | 2B | 50 | HPMCAS-HF | Mini |
| 6 | 3 | 10 | CAP | Mini |
| 7 | 3 | 10 | HPMCAS-MF | Mini |
| 8 | 4 | 50 | HPMCAS-MF | Niro PSD-1 |
| 9 | 1 | 10 | HPMC | Mini |
| 10 | 1 | 35 | CMEC | Niro PSD-1 |
| 11 | 1 | 20 | HPMCAS-MF | Mini |
| 12 | 1 | 25 | HPMCAS-MG | Niro PSD-1 |

HPMCAS-MF = medium fine grade (AQUAT-MF, Shin Etsu)
HPMCAS-HF = high, fine grade (AQUAT-HF, Shin Etsu)
HPMCAS-MG = medium, granular grade (AQUAT-MG, Shin Etsu)
CAP = cellulose acetate phthalate (NF grade, Eastman Chemical Co.)
HPMC = hydroxypropyl methyl cellulose (Methocel ®) Dow Chemical Co.
CMEC = carboxy methyl ethyl cellulose (Freund Industrial Co. Ltd., Tokyo, Japan)

Example 1

In this example, a method is used to screen a candidate lipophilic microphase-forming material for suitability in providing concentration-enhancement. A simulated intestinal buffer solution was prepared by dissolving 6.8 g of potassium phosphate monobasic in 750 mL of deionized water with 85 mL 0.2 M sodium hydroxide. Water was added for a final volume of 1 L. The pH was adjusted to 6.8±0.1 using 0.2 M sodium hydroxide.

Next, a lipophilic microphase-forming material was added to the buffer solution. 0.069 wt % polyethoxylated castor oil (CREMOPHOR RH40) and 0.031 wt % glyceryl mono- and di-caprylate (CAPMUL MCM) were added to the buffer to form the lipophilic microphase. 250 mL of the resulting solution was then added to a vessel in a VanKel dissolution testing apparatus with automatic sampling. The solution temperature was maintained at 37° C., and stirred with a paddle speed of 50 rpm.

After equilibration to 37° C., 120.3 mg of Dispersion 1 was added to the buffer containing the lipophilic microphase, resulting in a theoretical Drug 1 concentration of 120 μg/mL, if all of the drug had dissolved. Samples were collected at 5, 15, 20, 35, 45, 60, 75, 90, 120, 180 and 1200 minutes, centrifuged for 1 minute at 13,000 G, and then analyzed by high-performance liquid chromatography (HPLC) using a Waters Symmetry $C_8$ column. The mobile phase consisted of 0.2 vol % $H_3PO_4$ (in water)/methanol in the ratio of 15/85 vol/vol. Drug concentration was calculated by comparing UV absorbance at 256 nm to the absorbance of Drug 1 standards. Drug measured by HPLC includes free drug in solution, drug present in drug/polymer aggregates, and drug in the lipophilic microphase. The results are shown in Table 4.

Control 1

Control 1 consisted of dissolution of Dispersion 1 in intestinal buffer without the lipophilic microphase-forming material.

TABLE 4

| Example No. | Dispersion | Time (min) | Drug 1 Concentration (μg/mL) | AUC (min*μg/mL) |
|---|---|---|---|---|
| 1 | 1 | 0 | 0 | 0 |
|   |   | 5 | 42 | 100 |
|   |   | 15 | 75 | 700 |
|   |   | 20 | 85 | 1,100 |
|   |   | 35 | 86 | 2,400 |
|   |   | 45 | 87 | 3,200 |
|   |   | 60 | 84 | 4,500 |
|   |   | 75 | 85 | 5,800 |
|   |   | 90 | 81 | 7,000 |
|   |   | 120 | 78 | 9,400 |
|   |   | 180 | 74 | 14,000 |
|   |   | 1200 | 68 | 86,100 |
| Control 1 | 1 | 0 | 0 | 0 |
|   |   | 5 | 13 | 0 |
|   |   | 15 | 21 | 200 |
|   |   | 20 | 29 | 300 |
|   |   | 35 | 39 | 800 |
|   |   | 45 | 43 | 1,300 |
|   |   | 60 | 45 | 1,900 |
|   |   | 75 | 55 | 2,700 |
|   |   | 90 | 59 | 3,500 |
|   |   | 120 | 64 | 5,400 |
|   |   | 180 | 59 | 9,000 |
|   |   | 1200 | 40 | 59,400 |

The concentrations of drug obtained in these samples were used to determine the maximum concentration of drug ("$C_{max180}$") and the area under the concentration-versus-time curve ("$AUC_{180}$") during the initial one hundred eighty minutes. The results are shown in Table 5.

TABLE 5

| Exp. No. | Dispersion | Drug | Lipophilic Microphase | Lipophile/Drug Ratio | $C_{max180}$ (μg/mL) | $AUC_{180}$ (min*μg/mL) |
|---|---|---|---|---|---|---|
| 1 | 1 | 1 | Cremophor & Capmul | 8.3 | 87 | 14,000 |
| Control 1 | 1 | 1 | none | — | 64 | 9,000 |

As can be seen from the data, the test performed with the lipophilic microphase-forming material (Example 1) provided a $C_{max180}$ that was 1.4-fold that of the control, and an $AUC_{180}$ that was 1.6-fold that of the control, indicating that the lipophilic microphase-forming material is suitable for use in the invention.

Example 2

This example demonstrates that the lipophilic microphase forming material results in a significant amount of drug being present in lipophilic microphases and decreases the amount of drug present as precipitate. For Example 2, 4.0 mg of Dispersion 2 was added to Eppendorf tubes (in duplicate) containing 1.0 mL of deuterated PBS with the following lipophilic microphase-forming material: 1.09 mg Cremophore RH40 and 0.50 mg Capmul MCM. The solution also contained 0.11 mg 3-(trimethylsilyl)propionic-2,2,3,3-$d_4$ acid, sodium salt ("TSP"; a deuterated NMR reference standard). Next, 10 μL of a 1.11 mg/mL $^{19}$F trifluoroacetic acid standard solution ("TFA") was added to each tube. The solutions in the tubes were vortexed 1 minute, centrifuged 1 minute to remove bubbles, resuspended using a pipette, and transferred to an 8 mm NMR tube. Proton and $^{19}$F spectra were recorded for separate identical samples using a Varian Gemini 2000 NMR instrument. By comparing the drug NMR spectra to the TFA standard, these spectra were used to determine the total amount of Drug 1 present as free drug in solution and drug in the lipophilic microphase. Drug in polymer/drug assemblies was determined by subtracting the concentration of highly mobile drug from the concentration of total dissolved drug. Free drug and drug in the lipophilic microphase together are referred to as "highly mobile" drug.

The precipitate was analyzed by centrifuging the solution and decanting the supernatant. The pellet was dried, then dissolved in DMSO and analyzed by NMR. The proton spectra was used to measure the polymer:drug ratio, and the concentration of drug in the precipitate was calculated from standards.

HPLC was used to determine the amount of total dissolved drug in the supernatant following centrifugation. The drug observed by HPLC consisted of free drug in solution, drug present in polymer/drug assemblies, and drug in the lipophilic microphase.

The results of these tests were used to determine the amount of Drug 1 in precipitate, in highly mobile species, or in polymer/drug assemblies in a solution of Example 2. The results are shown in Table 6.

Control 2

Control 2 consisted of Dispersion 2 in deuterated PBS without the lipophilic microphase.

TABLE 6

| Exp. No. | Dispersion | Drug | Lipophilic Microphase | Lipophile/Drug Ratio | Drug in Precipitate (μg/mL) | Highly Mobile Drug (μg/mL) | Drug in Polymer/Drug Assemblies (μg/mL) |
|---|---|---|---|---|---|---|---|
| 2 | 2 | 1 | Cremophor & Capmul | 1.59 | 50 | 400 | 550 |
| Control 2 | 2 | 1 | none | — | 270 | <3 | 730 |

These data show that the composition of the present invention provided concentration enhancement over the control. Specifically, the concentration of drug that is highly mobile, meaning either present as free drug or present in lipophilic microphases, for Example 2 was at least 133-fold that provided by Control 2. In addition, the precipitate ratio was 5.4 (270/50).

Examples 3-8

These examples show concentration-enhancement provided by several candidate lipophilic microphase-forming materials. For each of Examples 3-8, Dispersion 2 was added to a solution containing a lipophilic microphase-forming material. Example 3 consisted of Dispersion 2 in solution with a mixture of sodium taurocholic acid and 1-palmitoyl-2-oleyl-sn-glycero-3-phosphocholine ("NaTC/POPC"; 4/1 wt/wt). Example 4 consisted of Dispersion 2 in solution with NaTC/POPC and a mixture of Tween 80 and Capmul MCM (40/60 wt/wt). Example 5 consisted of Dispersion 2 in solution with NaTC/POPC and a mixture of Cremophor RH40 and Capmul MCM (40/60 wt/wt). Example 6 consisted of Dispersion 2 in solution with NaTC/POPC and a mixture of Cremophor RH40 and Capmul MCM (72/28 wt/wt). Example 7 consisted of Dispersion 2 in solution with NaTC/POPC and a mixture of Cremophor RH40 and Arlacel 20 (75/25 wt/wt). Example 8 consisted of Dispersion 2 in solution with NaTC/POPC and sodium lauryl sulfate (SLS).

For Example 3, to analyze the concentration of Drug 1 that was highly mobile using NMR, 18 mg of Dispersion 2 was added to 1.8 mLs of deuterated PBS containing 0.5 wt % NaTC/POPC, and the reference standards TSP and $^{19}$F TFA. For Examples 4 through 8, 0.1 wt % of additional lipophilic microphase-forming materials were added. The results are shown in Table 7. Control 2 (Dispersion 2 in deuterated PBS without the lipophilic microphase) is shown again for comparison.

TABLE 7

| Ex. No. | Dispersion | Drug | Lipophilic Microphase | Lipophile/Drug Ratio | Highly Mobile Drug (μg/mL) |
|---|---|---|---|---|---|
| 3 | 2 | 1 | NaTC/POPC | 2.0 | 13.0 |
| 4 | 2 | 1 | NaTC/POPC + Tween 80 & Capmul | 2.4 | 24.9 |
| 5 | 2 | 1 | NaTC/POPC + Cremophor & Capmul (40/60) | 2.4 | 32.9 |
| 6 | 2 | 1 | NaTC/POPC + Cremophor & Capmul (72/28) | 2.4 | 86.7 |
| 7 | 2 | 1 | NaTC/POPC + Cremophor & Arlacel | 2.4 | 78.4 |

TABLE 7-continued

| Ex. No. | Dispersion | Drug | Lipophilic Microphase | Lipophile/Drug Ratio | Highly Mobile Drug (μg/mL) |
|---|---|---|---|---|---|
| 8 | 2 | 1 | NaTC/POPC + SLS | 2.4 | 22.8 |
| Control 2 | 2 | 1 | none | — | <1 |

The results show that addition of the lipophilic microphase results in greater than 13- to 86-fold increases in highly mobile drug concentrations compared with the control consisting of the dispersion alone. In addition, formulations with a lipophilic microphase-forming material inaddition to NaTC/POPC (examples 4 to 8), showed concentration enhancement over the use of NaTC/POPC alone (Example 3), with concentrations of highly mobile drug 1.7-fold to 6.7-fold that provided by Example 3.

Examples 9-12

These Examples demonstrate concentration enhancement using several different candidate lipophilic microphase-forming materials. In these examples, Dispersion 1 was co-administered to PBS containing the lipophilic microphase-forming material TWEEN 80 (Example 9), Capmul MCM (Example 10), Cremophor RH40 (Example 11), or a 69/31 (wt/wt) mixture of Cremophor RH40/Capmul MCM (Example 12).

For each of these tests, approximately 120 mg of Dispersion 1 was added to 250 mLs of PBS containing 0.5 wt % of the lipophilic microphase-forming material. Dissolution tests were performed as described for Example 1. Results are shown in Table 8.

TABLE 8

| Example No. | Dispersion | Time (min) | Drug 1 Concentration (µg/mL) | AUC (min*µg/mL) |
|---|---|---|---|---|
| 9 | 1 | 0 | 0 | 0 |
|   |   | 5 | 11 | 0 |
|   |   | 15 | 28 | 200 |
|   |   | 20 | 33 | 400 |
|   |   | 35 | 52 | 1,000 |
|   |   | 45 | 64 | 1,600 |
|   |   | 60 | 78 | 2,700 |
|   |   | 75 | 86 | 3,900 |
|   |   | 90 | 93 | 5,200 |
|   |   | 120 | 97 | 8,100 |
|   |   | 180 | 97 | 13,900 |
|   |   | 1200 | 91 | 110,000 |
| 10 | 1 | 0 | 0 | 0 |
|   |   | 5 | 73 | 200 |
|   |   | 15 | 89 | 1,000 |
|   |   | 20 | 90 | 1,400 |
|   |   | 35 | 94 | 2,800 |
|   |   | 45 | 94 | 3,800 |

TABLE 8-continued

| Example No. | Dispersion | Time (min) | Drug 1 Concentration (µg/mL) | AUC (min*µg/mL) |
|---|---|---|---|---|
|   |   | 60 | 94 | 5,200 |
|   |   | 75 | 91 | 6,600 |
|   |   | 90 | 90 | 7,900 |
|   |   | 120 | 84 | 10,500 |
|   |   | 180 | 75 | 15,300 |
|   |   | 1200 | 45 | 76,700 |
| 11 | 1 | 0 | 0 | 0 |
|   |   | 5 | 9 | 0 |
|   |   | 15 | 24 | 200 |
|   |   | 20 | 32 | 300 |
|   |   | 35 | 50 | 900 |
|   |   | 45 | 62 | 1,500 |
|   |   | 60 | 76 | 2,500 |
|   |   | 75 | 89 | 3,800 |
|   |   | 90 | 103 | 5,200 |
|   |   | 120 | 114 | 8,500 |
|   |   | 180 | 127 | 15,700 |
|   |   | 1200 | 144 | 153,800 |
| 12 | 1 | 0 | 0 | 0 |
|   |   | 5 | 49 | 100 |
|   |   | 15 | 92 | 800 |
|   |   | 20 | 101 | 1,300 |
|   |   | 35 | 111 | 2,900 |
|   |   | 45 | 112 | 4,000 |
|   |   | 60 | 113 | 5,700 |
|   |   | 75 | 112 | 7,400 |
|   |   | 90 | 112 | 9,100 |
|   |   | 120 | 113 | 12,500 |
|   |   | 180 | 111 | 19,200 |
|   |   | 1200 | 125 | 139,700 |

The concentrations of drug obtained in these samples were used to determine the $C_{max180}$ and the $AUC_{180}$ during the initial one hundred eighty minutes. The results are shown in Table 9. The result for Control 1 are shown again for comparison.

TABLE 9

| Exp. No. | Dispersion | Drug | Lipophilic Microphase | Lipophile/Drug Ratio | $C_{max180}$ (µg/mL) | $AUC_{180}$ (min*µg/mL) |
|---|---|---|---|---|---|---|
| 9 | 1 | 1 | Tween 80 | 41.7 | 97 | 13,900 |
| 10 | 1 | 1 | Capmul | 41.7 | 94 | 15,300 |
| 11 | 1 | 1 | Cremophor | 41.7 | 127 | 15,700 |
| 12 | 1 | 1 | Cremophor & Capmul | 41.7 | 113 | 19,200 |
| Control 1 | 1 | 1 | none | — | 64 | 9,000 |

As can be seen from the data, Examples 9 through 12 provided $C_{max180}$ from 1.5-fold to 2.0-fold that of the control, and $AUC_{180}$ from 1.5-fold to 2.1-fold that of the control.

Examples 13-15

These examples demonstrate concentration enhancement using Drug 2. The dispersions used in these Examples contained ziprazidone in either the hydrochloride salt form (Drug 2A), or the free base form (Drug 2B). Table 3 shows the compositions of Dispersions 3, 4, and 5 with Drug 2A or 2B. Examples 13 through 15 consisted of Dispersions 3 through 5 in solutions with NaTC/POPC as the lipophilic microphase.

For these tests, 3.6 mg of Dispersion 3, 0.78 mg of Dispersion 4, or 0.72 mg of Dispersion 5, was added to microcentrifuge tubes in duplicate. A sufficient amount of each dispersion was added so that the concentration of drug would have been approximately 200 μg/mL, if all of the drug had dissolved. The tubes were placed in a 37° C. temperature-controlled chamber, and 1.8 mL PBS containing 0.5 wt % NaTC/POPC was added to each respective tube. The samples were quickly mixed using a vortex mixer for about 60 seconds. The samples were centrifuged at 13,000 G at 37° C. for 1 minute. The resulting supernatant solution was then sampled and diluted 1:6 (by volume) with water/methanol (1/4) and then analyzed by high-performance liquid chromatography (HPLC) using a Phenomenex ODS 20 column. The mobile phase consisted of 0.02 M $KH_2PO_4$, pH 3.0/acetonitrile in the ratio of 60/40 vol/vol. Drug concentration was calculated by comparing UV absorbance at 254 nm to the absorbance of Drug 2A or 2B standards. The contents of each respective tube were mixed on the vortex mixer and allowed to stand undisturbed at 37° C. until the next sample was taken. Samples were collected at 4, 10, 20, 40, 90, and 1200 minutes. The results are shown in Table 10.

Controls 3-5

Controls 3 through 5 consisted of Dispersions 3 through 5, respectively, in PBS without the lipophilic microphase.

TABLE 10

| Example No. | Dispersion | Time (min) | Drug 2 Concentration (μg/mL) | AUC (min*μg/mL) |
|---|---|---|---|---|
| 13 | 3 | 0 | 0 | 0 |
| | | 4 | 173 | 300 |
| | | 10 | 168 | 1,400 |
| | | 20 | 133 | 2,900 |
| | | 40 | 108 | 5,300 |
| | | 90 | 59 | 9,500 |
| | | 1200 | 249 | 180,200 |
| 14 | 4 | 0 | 0 | 0 |
| | | 4 | 12 | 0 |
| | | 10 | 24 | 100 |
| | | 20 | 43 | 500 |
| | | 40 | 47 | 1,400 |
| | | 90 | 25 | 3,200 |
| | | 1200 | 15 | 25,800 |
| 15 | 5 | 0 | 0 | 0 |
| | | 4 | 74 | 100 |
| | | 10 | 42 | 500 |
| | | 20 | 37 | 900 |
| | | 40 | 21 | 1,500 |
| | | 90 | 16 | 2,400 |
| | | 1200 | 13 | 18,500 |
| Control 3 | 3 | 0 | 0 | 0 |
| | | 4 | 23 | 100 |
| | | 10 | 21 | 200 |
| | | 20 | 24 | 400 |
| | | 40 | 20 | 900 |
| | | 90 | 8 | 1,600 |
| | | 1200 | 8 | 10,900 |
| Control 4 | 4 | 0 | 0 | 0 |
| | | 4 | 10 | 0 |
| | | 10 | 13 | 100 |
| | | 20 | 16 | 200 |
| | | 40 | 13 | 500 |
| | | 90 | 9 | 1,100 |
| | | 1200 | 4 | 8,000 |
| Control 5 | 5 | 0 | 0 | 0 |
| | | 4 | 27 | 100 |
| | | 10 | 23 | 200 |
| | | 20 | 18 | 400 |
| | | 40 | 13 | 700 |
| | | 90 | 7 | 1,200 |
| | | 1200 | 7 | 8,500 |

The concentrations of drug obtained in these samples were used to determine the $C_{max90}$ and the initial ninety minutes. The results are shown in Table 11.

TABLE 11

| Ex. No. | Dispersion | Drug | Lipophilic Microphase | Lipophile/Drug Ratio | $C_{max90}$ (μg/mL) | $AUC_{90}$ (min*μg/mL) |
|---|---|---|---|---|---|---|
| 13 | 3 | 2A | NaTC/POPC | 25 | 173 | 9500 |
| Control 3 | 3 | 2A | none | — | 24 | 1600 |
| 14 | 4 | 2A | NaTC/POPC | 25 | 47 | 3200 |
| Control 4 | 4 | 2A | none | — | 16 | 1100 |
| 15 | 5 | 2A | NaTC/POPC | 25 | 74 | 2400 |
| Control 5 | 5 | 2A | none | — | 27 | 1200 |

As can be seen from the data, Examples 3, 4, and 5 provided $C_{max90}$ were 7.2-, 2.9-, and 2.7-fold that provided by each respective control. Examples 3, 4, and 5 provided $AUC_{90}$ values that were 5.9-, 2.9-, and 2.0-fold that provided by each respective control.

Examples 16-19

Examples 16 through 19 evaluate several lipophilic microphase-forming materials with dispersions containing different drugs and different polymers. Examples 16 through 19 consisted of Dispersions 6 through 9 in solutions with NaTC/POPC or Tween 80 as the lipophilic microphase material. Table 3 shows the compositions of Dispersions 6 through 9.

For Examples 16 and 17, 3.6 mg of Dispersion 6 or Dispersion 7 was added to PBS containing 2 wt % Tween 80 (the Drug 3 concentration would have been 200 μg/mL if all of the drug dissolved). For Example 18, 3.6 mg of Dispersion 8 was added to PBS containing 0.5 wt % NaTC/POPC (the Drug 4 concentration would have been 1000 μg/mL if all of the drug dissolved). For Example 19, 1.8 mg of Dispersion 9 was added to PBS containing 0.5 wt % NaTC/POPC (the Drug 1 concentration would have been 100 μg/mL if all of the drug dissolved). Dissolution tests were performed as described above for Examples 13 through 15. Drug 3 was analyzed by HPLC using a Waters Symmetry $C_{18}$ column. The mobile phase consisted of 0.02 M $KH_2PO_4$, pH 3.0/acetonitrile in the ratio of 60/40 vol/vol. Drug concentration was calculated by comparing UV absorbance at 208 nm to the absorbance of Drug 3 standards. Drug 4 was analyzed by HPLC using a Zorbax SB $C_{18}$ column. The mobile phase consisted of water/methanol in the ratio of 35/65 vol/vol. Drug concentration was calculated by comparing UV absorbance at 297 nm to the absorbance of Drug 4 standards. Drug 1 was analyzed by HPLC as described above for Example 1. Drug concentrations versus time are shown in Table 12.

Controls 6-9

Controls 6 through 9 consisted of Dispersions 6 through 9, respectively, in PBS without the lipophilic microphase-forming material.

TABLE 12

| Example No. | Dispersion | Time (min) | Drug Concentration (μg/mL) | AUC (min*μg/mL) |
| --- | --- | --- | --- | --- |
| 16 | 6 | 0 | 0 | 0 |
| | | 4 | 143 | 300 |
| | | 10 | 193 | 1300 |
| | | 20 | 206 | 3300 |
| | | 40 | 212 | 7500 |
| | | 90 | 207 | 18,000 |
| | | 1200 | 207 | 247,800 |
| 17 | 7 | 0 | 0 | 0 |
| | | 4 | 174 | 300 |
| | | 10 | 193 | 1,400 |
| | | 20 | 198 | 3,400 |
| | | 40 | 212 | 7,500 |
| | | 90 | 205 | 17,900 |
| | | 1200 | 217 | 252,200 |
| 18 | 8 | 0 | 0 | 0 |
| | | 4 | 1019 | 2,000 |
| | | 10 | 982 | 8,000 |
| | | 20 | 1004 | 18,000 |
| | | 40 | 970 | 37,700 |
| | | 90 | 961 | 86,000 |
| | | 1200 | 288 | 779,400 |
| 19 | 9 | 0 | 0 | 0 |
| | | 4 | 94 | 200 |
| | | 10 | 95 | 800 |
| | | 20 | 85 | 1,600 |
| | | 40 | 80 | 3,300 |
| | | 90 | 66 | 7,200 |
| | | 1200 | 28 | 63,800 |
| Control 6 | 6 | 0 | 0 | 0 |
| | | 4 | 159 | 300 |
| | | 10 | 149 | 1,200 |
| | | 20 | 148 | 2,700 |
| | | 40 | 130 | 5,500 |
| | | 90 | 117 | 11,700 |
| | | 1200 | 82 | 122,300 |
| Control 7 | 7 | 0 | 0 | 0 |
| | | 4 | 21 | 0 |
| | | 10 | 31 | 200 |
| | | 20 | 43 | 600 |
| | | 40 | 58 | 1,600 |
| | | 90 | 86 | 5,200 |
| | | 1200 | 173 | 148,900 |
| Control 8 | 8 | 0 | 0 | 0 |
| | | 4 | 540 | 1,100 |
| | | 10 | 582 | 4,400 |
| | | 20 | 601 | 10,400 |
| | | 40 | 620 | 22,600 |
| | | 90 | 594 | 52,900 |
| | | 1200 | 276 | 536,000 |
| Control 11 | 11 | 0 | 0 | 0 |
| | | 4 | 70 | 100 |
| | | 10 | 64 | 500 |
| | | 20 | 59 | 1,200 |
| | | 40 | 50 | 2,200 |
| | | 90 | 42 | 4,600 |
| | | 1200 | 18 | 37,800 |

The concentrations of drug obtained in these samples were used to determine the $C_{max90}$ and the $AUC_{90}$ during the initial ninety minutes. The results are shown in Table 13.

TABLE 13

| Ex. No. | Dispersion | Drug | Polymer | Lipophilic Microphase | Lipophile/Drug Ratio | $C_{max90}$ (μg/mL) | $AUC_{90}$ (min*μg/mL) |
| --- | --- | --- | --- | --- | --- | --- | --- |
| 16 | 6 | 3 | CAP | Tween | 100 | 212 | 18,000 |
| Control 6 | 6 | 3 | CAP | none | — | 159 | 11,700 |
| 17 | 7 | 3 | HPMCAS-MF | Tween | 100 | 212 | 17,900 |
| Control 7 | 7 | 3 | HPMCAS-MF | none | — | 86 | 5200 |
| 18 | 8 | 4 | HPMCAS-MF | NaTC/POPC | 5 | 1019 | 86,000 |
| Control 8 | 8 | 4 | HPMCAS-MF | none | — | 620 | 52,900 |
| 19 | 9 | 1 | HPMC | NaTC/POPC | 50 | 95 | 7200 |
| Control 9 | 9 | 1 | HPMC | none | — | 70 | 4600 |

As can be seen from the data, the Examples showed an improvement in $C_{max90}$ from 1.3- to 2.5-fold that of each respective control. The Examples showed an improvement in $AUC_{90}$ from 1.5- to 3.4-fold that of each respective control.

Example 20

Partition coefficients were measured for Drug 1 in PBS with the lipophilic microphase-forming materials Capmul MCM, a 2.2:1 (wt:wt) mixture of Cremophore RH40/Capmul MCM, Pluronic F127, TWEEN 80, sodium lauryl sulfate (SLS), PEG 6000 distearate, MYRJ 59, Cremophore A25, and NaTC/POPC, using the following method. First, highly mobile Drug 1 concentration was measured for solutions of crystalline Drug 1 and varying concentrations of the lipophilic microphase material, or with Dispersion 2 (25 wt % Drug 1 with HPMCAS-MF). The concentration of Drug 1 versus concentration of lipophilic microphase material was graphed, and the slope was used to determine the partition coefficient of Drug 1 in the lipophilic microphase material from the equation $$[Drug]_{lipophile} = [Drug]_{free} \cdot K_p \cdot \chi_{lipophile}$$

For example, to determine the partition coefficient for Drug 1 in a 2.2/1 w/w mixture of Cremophore RH40/Capmul MCM, 2.0 mg of crystalline Drug 1 was added to 2.0 mL of deuterated PBS containing $^{19}F$ TFA standard and 0.047 wt %, 0.089 wt %, or 0.164 wt % of a Cremophore RH40/Capmul MCM mixture (2.2/1 wt/wt). Each solution was stirred overnight at 37° C. Highly mobile Drug 1 concentration (free drug and drug in lipophilic microphases) was measured using NMR. The results are shown below in Table 14.

TABLE 14

| Cremophore/Capmul (wt %) | Highly-Mobile Drug 1 Concentration (μg/mL) |
|---|---|
| 0.047 | 9 |
| 0.089 | 23 |
| 0.164 | 53 |

The slope of the data in Table 14, $[Drug]_{lipophile} = [Drug]_{free} \cdot K_p \cdot \chi_{lipophile}$, is 38,000. Dividing this by $[Drug]_{free}$, 0.010 μg/mL, gives a partition coefficient, $K_p$, of 3,800,000. Partition coefficients for the remaining lipophilic microphase materials were calculated using similar procedures. The summary of partition coefficients is shown in Table 15.

TABLE 15

| Lipophilic Microphase Material | Partition Coefficient $K_p$ | |
|---|---|---|
| | Determined Using Crystalline Drug 1 | Determined Using Dispersion 2 |
| Capmul MCM | — | 11,000,000 |
| Cremophore RH40/Capmul MCM (2.2/1 wt/wt) | 3,800,000 | 4,700,000 |
| PEG 6000 distearate | — | 1,400,000 |
| Cremophore RH40 | — | 740,000 |
| Pluronic F127 | 400,000 | |
| Tween 80 | 320,000 | |
| MYRJ 59 | — | 300,000 |
| Cremophore A25 | — | 200,000 |

TABLE 15-continued

| Lipophilic Microphase Material | Partition Coefficient $K_p$ | |
|---|---|---|
| | Determined Using Crystalline Drug 1 | Determined Using Dispersion 2 |
| SLS | 63,000 | |
| NaTC/POPC | 33,000 | |

The data in Table 15 show that lipophilic microphase-forming materials with a wide range of partition coefficients with Drug 1 are available. The data also show that the partition coefficient measured for Drug 1 and a 2.2/1 (wt/wt) mixture of Cremophor RH40/Capmul MCM when using Dispersion 2 was greater than that measured when using crystalline Drug 1. This is because Dispersion 2 provides an enhanced free drug concentration ($[Drug]_{free}$) over crystalline Drug 1.

Example 21

Solutions containing Drug 1 in PBS with lipophilic microphase-forming materials were analyzed using light scattering to determine the size of the lipophilic microphases. To form these solutions, 3 mg Drug 1 was added to 10 mL PBS containing 0.1 wt % Capmul MCM/Tween 80 (3/2), or 0.1 wt % Cremophor RH40/Capmul MCM (5/2), and equilibrated overnight. Solutions were filtered using a 0.45 μm PTFE syringe filter to remove any undissolved species. Dynamic light-scattering of each of the solutions was measured using a PSS-NICOMP 380 Submicron Particle Sizer, and the size of lipophilic microphases in the solution was calculated. The mean particle sizes (characteristic diameter) for the bulk of particles in solution are shown in Table 16. (The value reported is a volume-weighted mean, assuming a gaussian size distribution, with approximately 85% of the particle volume being within about 30% of the reported size.)

TABLE 16

| Lipophilic Microphase (0.1 wt %) | Lipophile/Drug Ratio | DLS Mean Particle Size (nm) |
|---|---|---|
| Capmul MCM/Tween 80 (3/2) | 3.33 | 14.8 |
| Cremophor RH40/Capmul MCM (5/2) | 3.33 | 17.9 |

Example 22

The concentration-enhancement provided by Dispersion 11, comprising 20 wt % Drug 1, 20 wt % Capmul MCM, and 60 wt % HPMCAS-MF, was determined using NMR analysis as follows. A 9.0 mg sample of Dispersion was added to 1.8 mL of deuterated PBS, and the reference standards TSP and $^{19}F$ TFA, as described in Example 2. The concentration of highly mobile drug provided by Dispersion 11 as determined by NMR is shown in Table 17. For comparison, the results for Control 2 (Dispersion 2 comprising 25 wt % Drug 1 and 75 wt % HPMCAS-MF) is included in the table. These data show that the concentration of highly mobile Drug 1 provided by Dispersion 11, containing the lipophilic microphase-forming material Capmul MCM, was greater than 980-fold that provided by the control composition that did not contain the lipophilic microphase-forming material.

TABLE 17

| Example No. | Dispersion | Lipophilic Microphase-Forming Material | Lipophile/ Drug Ratio | Highly Mobile Drug 1 (µg/mL) |
|---|---|---|---|---|
| 22 | 11 | Capmul MCM (included in dispersion) | 1 | 980 |
| Control 2 | 2 | none | — | <1 |

Examples 23-25

The concentration-enhancement provided by Dispersion 2, comprising 25 wt % Drug 1 and 75 wt % HPMCAS when co-administered with various lipophilic microphase-forming materials was determined as follows. A 7.2 mg sample of Dispersion 2 was added to 1.8 mL of deuterated PBS, and the reference standards TSP and $^{19}$F TFA to which had been added 1.8 mg of the lipophilic microphase-forming materials shown in Table 18. The concentration of highly mobile drug provided by Dispersion 2 co-administered with these lipophilic microphase-forming materials was determined by NMR using the procedures outlined in Example 2. The results are presented in Table 18, as is the result for Control 2. These data show that the concentration of highly mobile Drug 1 provided by Dispersion 2 and the various lipophilic microphase-forming materials was greater than 2.4- to 360-fold that provided by the control composition that did not contain the lipophilic microphase-forming material.

TABLE 18

| Example No. | Dispersion | Lipophilic Microphase-Forming Material | Lipophile/ Drug Ratio | Highly Mobile Drug 1 (µg/mL) |
|---|---|---|---|---|
| 23 | 2 | PEG Distearate | 1 | 2.4 |
| 24 | 2 | Cremophor/Capmul (5/2 wt/wt) | 1 | 170 |
| 25 | 2 | Capmul MCM | 1 | 360 |
| Control 2 | 2 | None | — | <1 |

Examples 26-28

The concentration-enhancement provided by Dispersion 10, comprising 35 wt % Drug 1 and 65 wt % CMEC when co-administered with various lipophilic microphase-forming materials was determined as follows. A 5.1 mg sample of Dispersion 10 was added to 1.8 mL of deuterated PBS, and the reference standards TSP and $^{19}$F TFA to which had been added 1.8 mg of the lipophilic microphase-forming materials shown in Table 19. The concentration of highly mobile drug provided by Dispersion 10 co-administered with these lipophilic microphase-forming materials was determined by NMR using the procedures outlined in Example 2. The results are presented in Table 18, as is the result for Control 3, which comprised Dispersion 10 without a lipophilic microphase-forming material. These data show that the concentration of highly mobile Drug 1 provided by Dispersion 10 when co-administered with various lipophilic microphase-forming materials was greater than 3.4-fold to 210-fold that provided by the control composition that did not contain the lipophilic microphase-forming material.

TABLE 19

| Example No. | Dispersion | Lipophilic Microphase-Forming Material | Lipophile/ Drug Ratio | Highly Mobile Drug 1 (µg/mL) |
|---|---|---|---|---|
| 26 | 10 | PEG Distearate | 1 | 3.4 |
| 24 | 10 | Cremophor/Capmul (5/2 wt/wt) | 1 | 120 |
| 28 | 10 | Capmul MCM | 1 | 210 |
| Control 3 | 10 | none | — | <1 |

Example 29

This example demonstrates a lipophilic microphase-forming material adsorbed to a solid substrate.

The lipophilic microphase-forming material was adsorbed to a solid substrate as follows. First, a quantity of calcium silicate (Zeopharm® 600, available from JM Huber Corporation) was dried in a vacuum oven at a temperature of about 100° C. for 5 hours. Next a 69:31 (wt/wt) mixture of Cremophore RH 40:Capmul MCM was prepared. The materials were warmed sufficiently to become liquid, and 6.9 g of Cremophore RH 40 and 3.1 g of Capmul MCM was added to a vial. The mixture was warmed to 37° C. with constant stirring. The mixture was diluted by adding 10 g of methanol (1:1 mass ratio). The resulting solution was agitated and then stirred at room temperature. 1.1952 g of the Cremophore RH 40:Capmul MCM solution and 0.2015 g of calcium silicate were next added to a vial. The materials were mixed to form a slurry and then allowed to dry in a fume hood at room temperature overnight. The vials were then placed in a vacuum desiccator and allowed to dry for about five hours to remove residual methanol. The resulting material was a dry, freely flowing powder having a weight ratio of lipophilic microphase forming material to solid substrate of about 3/1.

Examples 30-31

Compositions comprising a solid amorphous dispersion and lipophilic-microphase forming material adsorbed onto a solid substrate were dissolution tested to determine whether the composition provided concentration-enhancement.

For Example 30, 7.2 mg of Dispersion 12 and 12 mg of the adsorbed lipophilic microphase-forming material of Example 29 was added to microcentrifuge tubes.

For Example 31, 3.6 mg of Dispersion 12 and 12 mg of the adsorbed lipophilic microphase-forming material of Example 29 was added to microcentrifuge tubes.

For Example 30, a sufficient amount of dispersion was added so that the concentration of drug would have been approximately 980 µg/mL, if all of the drug had dissolved. For Example 31, a sufficient amount of dispersion was added so that the concentration of drug would have been approximately 490 µg/mL, if all of the drug had dissolved. The tubes were placed in a 37° C. temperature-controlled chamber, and 1.8 mL MFDS was added to each respective tube. The samples were quickly mixed using a vortex mixer for about 90 seconds. The samples were centrifuged at 13,000 G at 37° C. for 2 minutes. The resulting supernatant solution was then sampled and diluted 1:5 (by volume) with methanol and then analyzed by HPLC. The contents of each respective tube were mixed on the vortex mixer and allowed to stand undisturbed at 37° C. until the next sample was taken. Samples were collected at 4, 10, 20, 40, 90, and 1200 minutes. The results are shown in Table 20.

Controls 10-13

Control 10 consisted of 7.2 mg of Dispersion 12 but no lipophilic microphase-forming material.

Control 11 consisted of 3.6 mg of Dispersion 12 but no lipophilic microphase-forming material.

Control 12 consisted of 1.8 mg of crystalline Drug 1 and 12 mg of the adsorbed lipophilic microphase-forming material of Example 29.

Control 13 consisted of 0.9 mg of crystalline Drug 1 and 12 mg of the adsorbed lipophilic microphase-forming material of Example 29.

TABLE 20

| Example No. | Dispersion | Time (min) | Drug 1 Concentration (µg/mL) | AUC (min*µg/mL) |
|---|---|---|---|---|
| 30 | 12 | 0 | 0 | 0 |
|  |  | 4 | 850 | 1,710 |
|  |  | 10 | 817 | 6,710 |
|  |  | 20 | 775 | 14,600 |
|  |  | 40 | 741 | 29,700 |
|  |  | 90 | 731 | 66,500 |
| 31 | 12 | 0 | 0 | 0 |
|  |  | 4 | 407 | 821 |
|  |  | 10 | 392 | 3,220 |
|  |  | 20 | 377 | 7,070 |
|  |  | 40 | 362 | 14,500 |
|  |  | 90 | 357 | 32,800 |
| Control 10 | 12 | 0 | 0 | 0 |
|  |  | 4 | 189 | 364 |
|  |  | 10 | 432 | 2,200 |
|  |  | 20 | 726 | 7,960 |
|  |  | 40 | 769 | 23,000 |
|  |  | 90 | 681 | 59,800 |
| Control 11 | 12 | 0 | 0 | 0 |
|  |  | 4 | 92 | 194 |
|  |  | 10 | 227 | 1,170 |
|  |  | 20 | 354 | 4,080 |
|  |  | 40 | 369 | 11,300 |
|  |  | 90 | 307 | 28,200 |
| Control 12 | none | 0 | 0 | 0 |
|  |  | 4 | 5 | 11 |
|  |  | 10 | 5 | 37 |
|  |  | 20 | 5 | 83 |
|  |  | 40 | 5 | 182 |
|  |  | 90 | 6 | 453 |
| Control 13 | none | 0 | 0 | 0 |
|  |  | 4 | 3 | 8 |
|  |  | 10 | 3 | 27 |
|  |  | 20 | 3 | 61 |
|  |  | 40 | 4 | 137 |
|  |  | 90 | 4 | 333 |

The concentrations of drug obtained in these samples were used to determine the $C_{max90}$ and the $AUC_{90}$ during the initial ninety minutes. The results are shown in Table 21.

TABLE 21

| Ex. No. | Dispersion | Drug | Lipophilic Microphase | Lipophile/ Drug Ratio | $C_{max90}$ (µg/mL) | $AUC_{90}$ (min*µg/mL) |
|---|---|---|---|---|---|---|
| 30 | 12 | 1 | Cremophor/ Capmul | 5 | 850 | 66,600 |
| Control 10 | 12 | 1 | none | — | 770 | 59,300 |
| Control 12 | none | 1 | Cremophor/ Capmul | 5 | 6 | 450 |
| 31 | 12 | 1 | Cremophor/ Capmul | 10 | 410 | 32,400 |
| Control 11 | 12 | 1 | none | — | 370 | 28,200 |
| Control 13 | none | 1 | Cremophor/ Capmul | 10 | 4 | 330 |

Combining a solid amorphous dispersion and adsorbed lipophilic microphase-forming material provided greatly enhanced drug concentration relative to controls consisting of equivalent amounts of crystalline drug and lipophilic microphase-forming material. As can be seen from the data, Example 30 provided a $C_{max90}$ that was 1.1- and 142-fold that provided by Controls 10 and 12 respectively. Example 31 provided a $C_{max90}$ that was 1.1- and 102-fold that provided by Controls 11 and 13, respectively. Example 30 provided an $AUC_{90}$ that was 1.1- and 148-fold that provided by Controls 10 and 12 respectively. Example 31 provided an $AUC_{90}$ that was 1.1- and 98-fold that provided by Controls 10 and 12 respectively.

Example 32

A combination of a solid amorphous dispersion and adsorbed lipophilic-microphase forming material was dosed to aqueous solution and analyzed by NMR using the procedure of Example 2 to determine the amount of highly mobile drug that was present in aqueous solution, compared with dosing a dispersion alone.

For Example 32, 7.2 mg of Dispersion 12 and 12 mg of the adsorbed lipophilic microphase-forming material of Example 29 were added to 1.8 ml of partially deuterated PBS containing 0.5 wt % NaTC/POPC and a TFA standard (0.0013M $^{19}$F). Samples were held at 37° C. and vortexed for one minute and then transferred to an 8 mm NMR tube. The concentration of drug was determined through integration of drug peaks and comparison with the TFA peaks.

Control 14 was the same as Example 32 but contained no adsorbed lipophilic microphase-forming material.

TABLE 22

| Ex. No. | Dispersion | Drug | Lipophilic Microphase | Lipophile/ Drug Ratio | Highly Mobile Drug (µg/mL) |
|---|---|---|---|---|---|
| 32 | 12 | 1 | Cremophor/ Capmul | 5 | 614 |
| Control 14 | 12 | 1 | none | — | 14 |

The results showed that addition of the lipophilic microphase forming material resulted in a 45-fold increase in highly mobile drug concentration compared with the control consisting of the dispersion alone.

The terms and descriptions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited by the claims which follow.

The invention claimed is:
1. A composition, comprising:
(a) a first solid amorphous dispersion comprising a low-solubility drug and a concentration-enhancing polymer, wherein said low-solubility drug is dispersed in said concentration-enhancing polymer, wherein said concentration-enhancing polymer is selected from the group consisting of hydroxypropyl methyl cellulose acetate succinate, hydroxypropyl methyl cellulose phthalate, cellulose acetate phthalate, cellulose acetate trimellitate, carboxymethyl ethyl cellulose, hydroxypropyl methyl cellulose, poloxamers, polyvinylpyrrolidone, polyvinyl alcohols that have at least a portion of their repeat units in hydrolyzed-form, and mixtures thereof; and
(b) a second solid adsorbate blended with the first solid amorphous dispersion, the solid adsorbate comprising a water immiscible lipophilic microphase-forming material adsorbed onto a porous substrate, the water immiscible lipophilic microphase forming material comprising a mixture of a hydrophobic material selected from medium-chain glycerol mono-, di-, and tri-alkylates, sorbitan esters, sorbitan fatty acid esters, or a mixture thereof, and an amphiphilic material selected from polyoxyethylene sorbitan fatty acid esters, alpha tocopheryl polyethylene glycol 1000 succinate, or mixtures thereof, said lipophilic microphase-forming material being capable of forming a separate phase within an in vitro or in vivo aqueous use environment; and
wherein said composition has a mass ratio of said lipophilic microphase-forming material to said low solubility drug of from 0.1 to 100; and wherein said lipophilic microphase-forming material is present in a sufficient amount so that said composition provides concentration enhancement of said drug in said aqueous use environment of at least 1.25-fold relative to both a first control composition and a second control composition, wherein (i) said first control composition consists essentially of an equivalent amount of said solid amorphous dispersion with no lipophilic microphase-forming a material present; and (ii) said second control composition consists essentially of an equivalent amount of said low-solubility drug in undispersed form with an equivalent amount of said lipophilic, microphase-forming material but with no concentration-enhancing polymer.

2. The composition of claim 1 wherein said lipophilic microphase-forming material forms lipophilic microphases in said use environment having a characteristic diameter of less than 10 µm.

3. The composition of claim 1 wherein said low-solubility drug has a solubility in said use environment of less than 10 µg/ml.

4. The composition of claim 1 wherein said lipophilic microphase forming material is selected from the group consisting of mixtures of medium-chain glyceryl mono-, di-, and/or tri-alkylates and alpha tocopheryl polyethylene glycol 1000 succinate, and mixtures of polyoxyethylene sorbitan fatty acid esters and medium-chain glyceryl mono-, di-, and/or tri-alkylates.

5. The composition of claim 1 wherein said lipophilic, microphase-forming material is dispersed in a water soluble or water dispersible matrix.

6. The composition of claim 1 wherein said lipophilic, microphase-forming material comprises from 10 wt % to 80 wt % of the composition.

7. The composition of claim 1 wherein said drug is a cholesterol ester transfer protein inhibitor.

8. The composition of claim 1 where said mass ratio of said lipophilic microphase-forming material to said low solubility drug is at least 1.

9. The composition of claim 1 wherein said composition provides a dissolution area under the curve in a use environment for any 90-minute period between the time of introduction to the use environment and 270 minutes following introduction to the use environment that is at least 1.25-fold that provided by at least one of said first control composition and said second control composition.

10. The composition of claim 1 wherein said composition provides a fed/fasted relative bioavailability ratio of from 0.5 to 2.0.

11. The composition of claim 1 wherein said drug is selected from the group consisting of antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents, glycogen phosphorylase inhibitors, and cholesterol ester transfer protein inhibitors.

12. A composition, comprising:
a first solid amorphous dispersion comprising a low-solubility drug dispersed in a concentration-enhancing polymer, the low-solubility drug having a solubility in an in vitro or in vivo aqueous use environment of less than 10 µg/ml, the low-solubility drug being selected from antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesterol ester transfer protein inhibitors, the concentration-enhancing polymer being selected from the group consisting of hydroxypropyl methyl cellulose acetate succinate, hydroxypropyl methyl cellulose phthalate, cellulose acetate phthalate, cellulose acetate trimellitate, carboxymethyl ethyl cellulose, hydroxypropyl methyl cellulose, poloxamers, polyvinylpyrrolidone, polyvinyl alcohols that have at least a portion of their repeat units in hydrolyzed-form, and mixtures thereof; and
a second solid adsorbate comprising a water immiscible lipophilic microphase-forming material adsorbed onto a porous substrate, the water immiscible lipophilic microphase forming material comprising a mixture of a hydrophobic material and an amphiphilic material, the lipophilic microphase-forming material being capable of forming a separate phase within the in vitro or in vivo aqueous use environment, the composition having a mass ratio of the lipophilic microphase-forming material to the low solubility drug of from 0.1 to 100, the lipophilic microphase-forming material being present in an amount sufficient to provide concentration enhancement of the drug in the aqueous use environment of at least 1.25-fold relative to both a first control composition and a second control composition, wherein (i) the first control composition consists essentially of an equivalent amount of the solid amorphous dispersion with no lipophilic microphase-forming a material present, and (ii) the second control composition consists essentially of an equivalent amount of the low-solubility drug in undispersed form with an equivalent amount of the lipophilic, microphase-forming material but with no concentration-enhancing polymer.

13. A method, comprising:
forming a first solid amorphous dispersion comprising a low-solubility drug homogeneously dispersed in a concentration-enhancing polymer selected from the group consisting of hydroxypropyl methyl cellulose acetate succinate, hydroxypropyl methyl cellulose phthalate, cellulose acetate phthalate, cellulose acetate trimellitate, carboxymethyl ethyl cellulose, hydroxypropyl methyl cellulose, poloxamers, polyvinylpyrrolidone, polyvinyl alcohols that have at least a portion of their repeat units in hydrolyzed-form, and mixtures thereof;
forming a second solid adsorbate by adsorbing a water immiscible lipophilic microphase-forming material capable of forming a separate phase within an in vitro or in vivo aqueous use environment onto a porous substrate; and
forming a composition comprising the first solid amorphous dispersion and the second solid adsorbate, the composition having a mass ratio of the lipophilic microphase-forming material to the low solubility drug of from 0.1 to 100, the lipophilic microphase-forming material being present in a sufficient amount so that the composition provides concentration enhancement of the drug in the aqueous use environment of at least 1.25-fold relative to both a first control composition and a second control composition, wherein (i) the first control composition consists essentially of an equivalent amount of the solid amorphous dispersion with no lipophilic microphase-forming a material present; and (ii) the second control composition consists essentially of an equivalent amount of the low-solubility drug in undispersed form with an equivalent amount of the lipophilic, microphase-forming material but with no concentration-enhancing polymer.

14. The method according to claim 13 where the first solid amorphous dispersion comprising a low-solubility drug homogeneously dispersed in a concentration-enhancing polymer is formed by spray drying.

* * * * *